US012631553B2

(12) United States Patent     (10) Patent No.:   US 12,631,553 B2

Van Hal et al.     (45) Date of Patent:     May 19, 2026

(54) PREDICTION OF PERCENTAGE LEVELS OF GASES THAT ARE UNDETECTABLE VIA OPTICAL ABSORPTION MEASUREMENTS

(71) Applicant: Schlumberger Technology Corporation, Sugar Land, TX (US)

(72) Inventors: Ronald E. G. Van Hal, Cambridge, MA (US); Victoria Skates, Cambridge, MA (US); Shawn David Taylor, Cambridge, MA (US)

(73) Assignee: Schlumberger Technology Corporation, Sugar Land, TX (US)

( * ) Notice: Subject to any disclaimer, the term of this patent is extended or adjusted under 35 U.S.C. 154(b) by 0 days.

(21) Appl. No.: 19/121,444

(22) PCT Filed: Nov. 29, 2023

(86) PCT No.: PCT/US2023/081597

§ 371 (c)(1),
(2) Date: Apr. 16, 2025

(87) PCT Pub. No.: WO2024/118770

PCT Pub. Date: Jun. 6, 2024

(65)      Prior Publication Data

US 2026/0110631 A1     Apr. 23, 2026

Related U.S. Application Data

(60) Provisional application No. 63/385,351, filed on Nov. 29, 2022.

(51) Int. Cl.
*G01N 21/3504*     (2014.01)
*E21B 49/08*     (2006.01)
(Continued)

(52) U.S. Cl.
CPC ......... *G01N 21/3504* (2013.01); *E21B 49/08* (2013.01); *G01N 1/14* (2013.01);
(Continued)

(58) Field of Classification Search
None
See application file for complete search history.

(56)      References Cited

U.S. PATENT DOCUMENTS 4,994,671 A    2/1991   Safinya
5,167,149 A    12/1992   Mullins
(Continued)

FOREIGN PATENT DOCUMENTS

WO     2004083833 A1    9/2004
WO     2024118790 A1    6/2024

OTHER PUBLICATIONS

International Search Report and Written Opinion of International Patent Application No. PCT/US2023/081597 dated on Mar. 25, 2024, 10 pages.
(Continued)

*Primary Examiner* — Marcus H Taningco
(74) *Attorney, Agent, or Firm* — Jeffrey D. Frantz

(57)      ABSTRACT

Systems and methods of the present disclosure include a fluid sampling system that includes a fluid sampling tool and a controller. The fluid sampling tool includes a probe configured to draw a fluid from a formation within which the fluid sampling tool is disposed during an oil and gas well operation. The fluid sampling tool also includes a spectrometer configured to detect raw data relating to optical properties of the fluid. The raw data relating to the optical properties of the fluid includes optical absorbance at a plurality of wavelengths. The controller includes at least one processor configured to execute coded instructions stored in memory of the controller, wherein the coded instructions,
(Continued)

when executed by the at least one processor, cause the processor to receive the raw data relating to the optical properties of the fluid from the spectrometer, and to predict percentage levels of one or more components in the fluid based at least in part on the raw data relating to the optical properties of the fluid. The one or more components comprise at least one gas component without an optical signature in the near infrared spectrum.

16 Claims, 15 Drawing Sheets

(51) Int. Cl.

| | |
|---|---|
| *G01N 1/14* | (2006.01) |
| *G01N 21/3577* | (2014.01) |
| *G01N 21/359* | (2014.01) |
| *G01N 33/28* | (2006.01) |

(52) U.S. Cl.
CPC ....... *G01N 21/3577* (2013.01); *G01N 21/359* (2013.01); *G01N 33/2823* (2013.01); *G01N 33/2841* (2013.01)

(56) References Cited

U.S. PATENT DOCUMENTS

| | | | |
|---|---|---|---|
| 5,266,880 | A | 11/1993 | Newland |
| 5,331,156 | A | 7/1994 | Hines |
| 5,859,430 | A | 1/1999 | Mullins |
| 5,939,717 | A * | 8/1999 | Mullins .............. G01N 21/3504 |
| | | | 250/269.1 |
| 6,274,865 | B1 | 8/2001 | Schroer |
| 8,686,364 | B1 | 4/2014 | Little, III |
| 10,151,738 | B2 | 12/2018 | Iyer |
| 10,718,747 | B2 | 7/2020 | Pelletier |
| 2009/0143992 | A1 * | 6/2009 | Fujisawa ............ G01N 33/2823 |
| | | | 702/13 |
| 2010/0282959 | A1 * | 11/2010 | Dong ........................ G01V 8/02 |
| | | | 250/269.1 |
| 2013/0071934 | A1 | 3/2013 | Indo |
| 2014/0360257 | A1 * | 12/2014 | Indo ........................ E21B 49/10 |
| | | | 73/152.28 |
| 2016/0161462 | A1 * | 6/2016 | Iyer .................... G01N 33/0036 |
| | | | 702/6 |
| 2016/0273354 | A1 | 9/2016 | Chen |
| 2017/0370214 | A1 * | 12/2017 | Wang ................. E21B 49/0875 |
| 2020/0124584 | A1 | 4/2020 | Morgan |
| 2020/0348444 | A1 | 11/2020 | Chen |
| 2022/0074303 | A1 | 3/2022 | Molla |

OTHER PUBLICATIONS

Guo, S. et al., "New Innovative Methods to Predict N2 in Real Time: Expand New Wireline Formation Testing Platform Products to Fit Basins", OTC-31487-MS, prepared for presentation af the Offshore Technology Conference Asia, Kuala Lumpur, Malaysia, 2022, 14 pages.

* cited by examiner

Figures 6A, 6B:
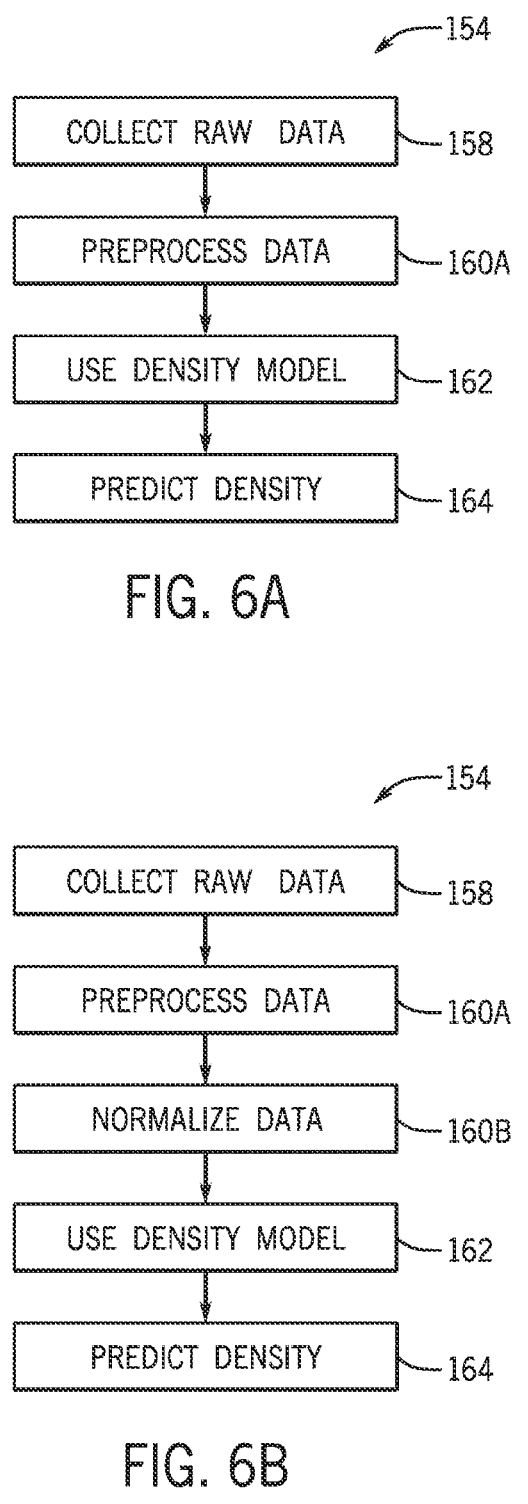

—154

COLLECT RAW DATA —158

PREPROCESS DATA —160A

USE DENSITY MODEL —162

PREDICT DENSITY —164

COLLECT RAW DATA —158

PREPROCESS DATA —160A

NORMALIZE DATA —160B

USE DENSITY MODEL —162

PREDICT DENSITY —164

PREDICTION OF PERCENTAGE LEVELS OF GASES THAT ARE UNDETECTABLE VIA OPTICAL ABSORPTION MEASUREMENTS

CROSS-REFERENCE TO RELATED APPLICATIONS

The present patent application is the National Stage Entry of International Application No. PCT/US2023/081597, filed on Nov. 29, 2023, that claims priority to U.S. Provisional Patent Application No. 63/385,351 that was filed on Nov. 29, 2022, which is herein incorporated by reference in its entirety.

FIELD OF THE INVENTION

The present disclosure relates to systems and methods for predicting mass density based on optical absorbance at various wavelengths in the near infrared spectrum, and for predicting percentage levels of gases without an optical signature in the near infrared spectrum.

BACKGROUND INFORMATION

Wells are generally drilled into subsurface rocks to access fluids, such as hydrocarbons, stored in subterranean formations. The formations penetrated by a well can be evaluated for various purposes including for identifying hydrocarbon reservoirs within the formations. During drilling operations, one or more drilling tools in a drill string may be used to test or sample the formations. Following removal of the drill string, a wireline tool may also be run into the well to test or sample the formations. These drilling tools and wireline tools, as well as other wellbore tools conveyed on coiled tubing, drill pipe, casing or other means of conveyance, are also referred to herein as "downhole tools." Certain downhole tools may include two or more integrated collar assemblies, each for performing a separate function, and a downhole tool may be employed alone or in combination with other downhole tools in a downhole tool string.

Formation evaluation may involve drawing fluid from the formation into a downhole tool. In some instances, the fluid drawn from the formation is retained within the downhole tool for later testing outside of the well. In other instances, downhole fluid analysis may be used to test the fluid while it remains in the well. Such analysis can be used to provide information on certain fluid properties in real time without the delay associated with returning fluid samples to the surface.

SUMMARY

A summary of certain embodiments described herein is set forth below. It should be understood that these aspects are presented merely to provide the reader with a brief summary of these certain embodiments and that these aspects are not intended to limit the scope of this disclosure.

In addition, certain embodiments of the present disclosure include a fluid sampling system that includes a fluid sampling tool and a controller. The fluid sampling tool includes a probe configured to draw a fluid from a formation within which the fluid sampling tool is disposed during an oil and gas well operation. The fluid sampling tool also includes a spectrometer configured to detect raw data relating to optical properties of the fluid. The raw data relating to the optical properties of the fluid includes optical absorbance at a plurality of wavelengths. The controller includes at least one processor configured to execute coded instructions stored in memory of the controller, wherein the coded instructions, when executed by the at least one processor, cause the processor to receive the raw data relating to the optical properties of the fluid from the spectrometer, and to predict percentage levels of one or more components in the fluid based at least in part on the raw data relating to the optical properties of the fluid. The one or more components comprise at least one gas component without an optical signature in the near infrared spectrum.

Further, certain embodiments of the present disclosure include a method. The method includes disposing a fluid sampling tool within a wellbore; drawing fluid from a formation within the wellbore, within which the fluid sampling tool is disposed, using a probe. The method further includes detecting raw data relating to optical properties of the fluid using a spectrometer, wherein the raw data relating to the optical properties of the fluid comprises optical absorbance at a plurality of wavelengths. Further, the method further includes receiving, by a controller, the raw data relating to optical properties of the fluid from the spectrometer, wherein the controller comprises at least one processor configured to execute coded instruction stored in a memory of the controller. Additionally, the method further includes predicting, by the controller, percentage levels of one or more components in the fluid based at least in part on the raw data relating to the optical properties of the fluid, wherein the one or more components comprise at least one gas component without an optical signature in the near infrared spectrum.

Various refinements of the features noted above may exist in relation to various aspects of the present embodiments. Further features may also be incorporated in these various aspects as well. These refinements and additional features may exist individually or in any combination. For instance, various features discussed below in relation to the illustrated embodiments may be incorporated into any of the above-described aspects of the present disclosure alone or in any combination. Again, the brief summary presented above is intended just to familiarize the reader with certain aspects and contexts of some embodiments without limitation to the claimed subject matter.

BRIEF DESCRIPTION OF THE DRAWINGS

Various aspects of this disclosure may be better understood upon reading the following detailed description and upon reference to the drawings, in which:

FIGS. 6A and 6B are flow diagrams of a first method (with two alternate routes) to predict mass density of a sample formation fluid, in accordance with embodiments of the present disclosure;

DETAILED DESCRIPTION

Figure 1:
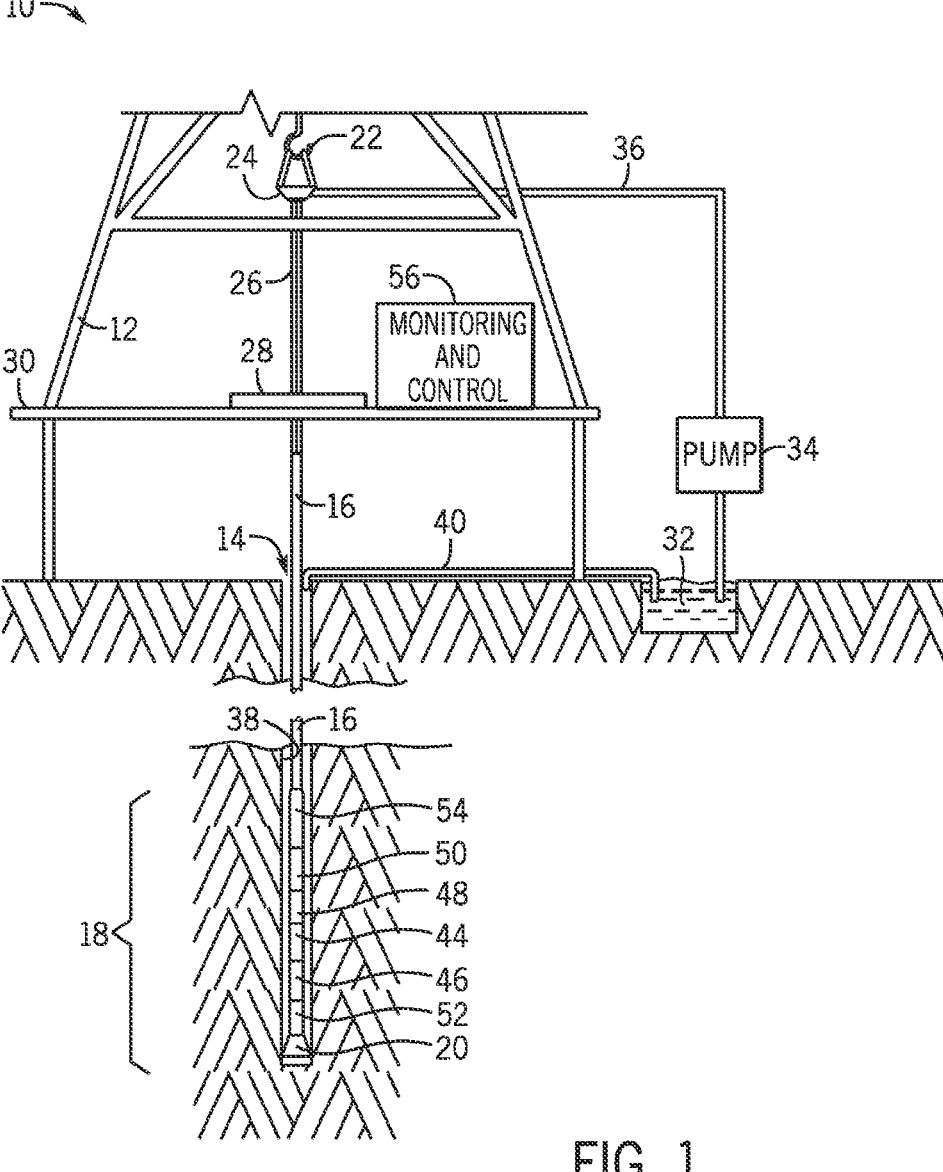
FIG. 1 illustrates a drilling system having a fluid sampling tool in a drill string, in accordance with embodiments of the present disclosure.

In the following, reference is made to embodiments of the disclosure. It should be understood, however, that the disclosure is not limited to specific described embodiments. Instead, any combination of the following features and elements, whether related to different embodiments or not, is contemplated to implement and practice the disclosure. Furthermore, although embodiments of the disclosure may achieve advantages over other possible solutions and/or over the prior art, whether or not a particular advantage is achieved by a given embodiment is not limiting of the disclosure. Thus, the following aspects, features, embodiments and advantages are merely illustrative and are not considered elements or limitations of the claims except where explicitly recited in a claim. Likewise, reference to "the disclosure" shall not be construed as a generalization of inventive subject matter disclosed herein and should not be considered to be an element or limitation of the claims except where explicitly recited in a claim.

Although the terms first, second, third, etc., may be used herein to describe various elements, components, regions, layers and/or sections, these elements, components, regions, layers and/or sections should not be limited by these terms. These terms may be only used to distinguish one element, component, region, layer or section from another region, component, region, layer or section. Terms such as "first", "second" and other numerical terms, when used herein, do not imply a sequence or order unless clearly indicated by the context. Thus, a first element, component, region, layer or section discussed herein could be termed a second element, component, region, layer or section without departing from the teachings of the example embodiments.

When introducing elements of various embodiments of the present disclosure, the articles "a," "an," and "the" are intended to mean that there are one or more of the elements. The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional embodiments that also incorporate the recited features.

When an element or layer is referred to as being "on," "engaged to," "connected to," or "coupled to" another element or layer, it may be directly on, engaged, connected, coupled to the other element or layer, or interleaving elements or layers may be present. In contrast, when an element is referred to as being "directly on," "directly engaged to," "directly connected to," or "directly coupled to" another element or layer, there may be no interleaving elements or layers present. Other words used to describe the relationship between elements should be interpreted in a like fashion. As used herein, the term "and/or" includes any and all combinations of one or more of the associated listed terms.

Some embodiments will now be described with reference to the figures. Like elements in the various figures will be referenced with like numbers for consistency. In the following description, numerous details are set forth to provide an understanding of various embodiments and/or features. It will be understood, however, by those skilled in the art, that some embodiments may be practiced without many of these details, and that numerous variations or modifications from the described embodiments are possible. As used herein, the terms "above" and "below", "up" and "down", "upper" and "lower", "upwardly" and "downwardly", and other like terms indicating relative positions above or below a given point are used in this description to more clearly describe certain embodiments.

In addition, as used herein, the terms "real time", "real-time", or "substantially real time" may be used interchangeably and are intended to describe operations (e.g., computing operations) that are performed without any human-perceivable interruption between operations. For example, as used herein, data relating to the systems described herein may be collected, transmitted, and/or used in control computations in "substantially real time" such that data readings, data transfers, and/or data processing steps occur once every second, once every 0.1 second, once every 0.01 second, or even more frequent, during operations of the systems (e.g., while the systems are operating). In addition, as used herein, the terms "continuous", "continuously", or "continually" are intended to describe operations that are performed without any significant interruption. For example, as used herein, control commands may be transmitted to certain equipment every five minutes, every minute, every 30 seconds, every 15 seconds, every 10 seconds, every 5 seconds, or even more often, such that operating parameters of the equipment may be adjusted without any significant interruption to the closed-loop control of the equipment. In addition, as used herein, the terms "automatic", "automated", "autonomous", and so forth, are intended to describe operations that are performed or caused to be performed, for example, by a computing system (i.e., solely by the computing system, without human intervention). Indeed, it will be appreciated that the control system described herein may be configured to perform any and all of the control functions described herein automatically.

In addition, as used herein, the term "substantially similar" may be used to describe values that are different by only a relatively small degree relative to each other. For example, two values that are substantially similar may be values that are within 10% of each other, within 5% of each other, within 3% of each other, within 2% of each other, within 1% of each other, or even within a smaller threshold range, such as within 0.5% of each other or within 0.1% of each other.

Similarly, as used herein, the term "substantially parallel" may be used to define downhole tools, formation layers, and so forth, that have longitudinal axes that are parallel with each other, only deviating from true parallel by a few degrees of each other. For example, a downhole tool that is substantially parallel with a formation layer may be a downhole tool that traverses the formation layer parallel to a boundary of the formation layer, only deviating from true parallel relative to the boundary of the formation layer by less than 5 degrees, less than 3 degrees, less than 2 degrees, less than 1 degree, or even less.

The present disclosure generally relates to downhole fluid analysis using optical spectroscopy. In particular, the embodiments described herein provide new methods to predict mass density based on optical absorbance at various wavelengths in the near infrared spectrum (e.g., from 780 nanometers to 2500 nanometers). In particular, the embodiments described herein include two methods to predict formation fluid mass density based on a detected optical spectrum. For example, a first method uses a model to predict the mass density directly from the optical spectrum. In a second method, a first model is used to predict the compositions of hydrocarbon components followed by a second model to predict the mass density based on the compositions. The models may either be physics-based models, statistical models, machine learning models, or artificial neural networks.

In addition, the embodiments described herein provide three methods to predict percentage levels of gases without an optical signature in the near infrared spectrum (e.g., hydrogen sulfide, nitrogen, helium, hydrogen in a hydrocarbon layer). In particular, the embodiments described herein include three methods to determine an amount of gas that is not directly measurable by the optics. A first method makes use of predicted mass density by the raw optical data and the predicted mass density based on the predicted composition and pressure and temperature. The difference may then be used to predict the amount of undetectable gas. A second method makes use of a predicted mass density based on the raw optical data and a predicted mass density based on normalized optical data. The difference may then be used to predict the amount of undetectable gas. A third method makes use of a measured optical density and a predicted optical density based on the pressure and temperature and predicted composition. The difference may then be used to predict the amount of undetectable gas. Furthermore, the embodiments described herein provide a method to determine the molar mass of the gas, thus identifying the gas.

Near-infrared spectroscopy has proven to be a valuable tool for characterizing the composition of reservoir fluids in a hydrocarbon-bearing formation. Using only the transmission of light through an optical path (e.g., typically about 2 mm), a great deal of information may be inferred about the composition of a hydrocarbon fluid. These techniques have been vital for understanding reservoir fluids.

A relatively early patent to describe such instrumentation and measurement was by Safinya and Tarvin (U.S. Pat. No. 4,994,671). Many more patents followed this original patent including, but not limited to, detecting the presence of gas (Mullins; U.S. Pat. No. 5,167,149), differentiating between oils (Mullins; U.S. Pat. No. 5,266,880), analyzing oil and water flow streams (Hines; U.S. Pat. No. 5,331,156), compositional analysis of gases (Mullins; U.S. Pat. No. 5,859,430), and methods to quantitate OBM filtrate contamination (Schroer; U.S. Pat. No. 6,274,865).

Over the years, various downhole tools have been developed with each new downhole tool providing better resolution on the composition of the hydrocarbon fluids. After the initial $C_1$, $C_2$-$C_5$, $C_{6+}$, and $CO_2$ algorithms, an improved algorithm distinguishing $C_2$ separately was developed. In general, the $C_3$ to $C_5$ fractions may further be separated in $C_3$, $C_4$, and $C_5$.

New tool developments have made the measurement stability of downhole tools better and more precise. However, there are situations where one or more elements of the downhole tool give erroneous measurements due to fouling or other circumstances. For example, the mass density measurement may be sensitive to fouling while in gas but also in cases where water droplets are stuck to the sensors. Techniques developed to clean the sensors downhole have not always been successful. Furthermore, the sensors may fail during operation due to unforeseen circumstances.

In addition, the presence of gases without an optical signature in the near infrared spectrum may not be detected using conventional algorithms. The presence of percentage level concentrations of nitrogen, helium, hydrogen, or hydrogen sulfide may affect the financial value of the gases and ultimately the viability of producing a particular field. Therefore, the importance of providing at least an indication of the presence and the concentration of these gases has been recognized, especially if a specific gas is known to be present in a particular formation.

As an example, in certain fields, substantial concentration of nitrogen are experienced, requiring real time prediction of nitrogen. Many different types of methods have been suggested, including a basin-specific approach based on established relations between light hydrocarbons and nitrogen and between carbon dioxide and nitrogen. This method cannot be universally applied but is modified for every basin using information that was obtained from other wells in the same zone. A second method makes an iteration between the optical composition and the measured density. This method begins with an estimate of nitrogen based on the above method followed by several iterations to predict the nitrogen concentration. This method is dependent on the quality of the density measurement. As such, poor density measurement due to fouling of the sensors may result in relatively large errors. In a third method, an equation of state (EOS) may be used to calculate the density. Starting from a fluid composition without nitrogen, nitrogen is added until the density calculated with the EOS matches the predicted density. After each addition, the total composition may be rebalanced to 100%. This method is again dependent on an accurate measurement of the density.

Pelletier et al. (U.S. Pat. No. 10,718,747) describe a method to determine the presence of inorganic gases in a formation fluid. In one method, the fluid sample may be flashed in a downhole tool, and the density of the flashed gas may be measured using a pycnometer. Another suggested method to determine the density is the use of a series of pressure points over a measured depth difference. The density may be calculated by the slope of pressure versus depth. The density may then be matched with the density calculated from the organic components and the unknown inorganic component. This gives a value for missing density, which is the molar weight multiplied by the mole fraction of the inorganic component. Disadvantages of this method is that a flashed gas is needed and that the carbon dioxide concentration is part of the unknown inorganic component.

Using the embodiments described herein, the presence of a non-carbon gas may be inferred from pressure, temperature, and optical measurements, without the need for a mass density measurement. However, the mass density measurement may be used to determine the molar mass of the unknown gas.

Turning now to the drawings, a drilling system 10 is illustrated in FIG. 1. As illustrated, the drilling system 10 includes a drilling rig 12 positioned over a well 14. Although illustrated as an onshore drilling system 10, it is noted that the drilling system could instead be an offshore drilling system. In certain embodiments, the drilling rig 12 supports a drill string 16 that includes a bottomhole assembly 18 having a drill bit 20. The drilling rig 12 may rotate the drill string 16 (and its drill bit 20) to drill the well 14 illustrated in FIG. 1.

In certain embodiments, the drill string 16 may be suspended within the well 14 from a hook 22 of the drilling rig 12 via a swivel 24 and a kelly 26. Although not illustrated in FIG. 1, it will be appreciated that the hook 22 may be connected to a hoisting system used to raise and lower the drill string 16 within the well 14. As but one non-limiting example, such a hoisting system may include a crown block and a drawworks that cooperate to raise and lower a traveling block (to which the hook 22 is connected) via a hoisting line. The kelly 26 is coupled to the drill string 16, and the swivel 24 allows the kelly 26 and the drill string 16 to rotate with respect to the hook 22. In certain embodiments, a rotary table 28 on a drill floor 30 of the drilling rig 12 may be configured to grip and turn the kelly 26 to drive rotation of the drill string 16 to drill the well 14. In other embodiments, however, a top drive system may instead be used to drive rotation of the drill string 16.

During operation, drill cuttings or other debris may collect near the bottom of the well 14. Drilling fluid 32, also referred to as drilling mud, may be circulated through the well 14 to remove this debris. The drilling fluid 32 may also clean and cool the drill bit 20 and provide positive pressure within the well 14 to inhibit formation fluids from entering the wellbore. In the embodiment illustrated in FIG. 1, the drilling fluid 32 is circulated through the well 14 by a pump 34. In addition, the drilling fluid 32 is pumped from a mud pit (or some other reservoir, such as a mud tank) into the drill string 16 through a supply conduit 36, the swivel 24, and the kelly 26. In general, the drilling fluid 32 exits near the bottom of the drill string 16 (e.g., at the drill bit 20) and returns to the surface through the annulus 38 between the wellbore and the drill string 16. A return conduit 40 may transfer the returning drilling fluid 32 away from the well 14. In certain embodiments, the returning drilling fluid 32 may be cleansed (e.g., via one or more shale shakers, desanders, or desilters) and reused in the well 14.

In addition to the drill bit 20, the bottomhole assembly 18 may also include various instruments that measure information of interest within the well 14. For example, as illustrated in FIG. 1, the bottomhole assembly 18 may include a logging-while-drilling (LWD) module 44 and a measurement-while-drilling (MWD) module 46. Both modules 44, 46 may include sensors that collect data and enable the creation of measurement logs in real-time during a drilling operation. The modules 44, 46 also include memory devices for storing the measured data. The LWD module 44 includes sensors that measure various characteristics of the rock and formation fluid properties within the well 14. Data collected by the LWD module 44 may include measurements of gamma rays, resistivity, neutron porosity, formation density, sound waves, optical density, and the like. The MWD module 46 includes sensors that measure various characteristics of the bottomhole assembly 18 and the wellbore, such as orientation (azimuth and inclination) of the drill bit 20, torque, shock and vibration, the weight on the drill bit 20, and downhole temperature and pressure. The data collected by the MWD module 46 may be used to control drilling operations. The bottomhole assembly 18 may also include one or more additional modules 48, which could be LWD modules, MWD modules, or other types of downhole data collection modules. It is noted that the bottomhole assembly 18 is modular, and that the positions and presence of particular modules 44, 46, 48 of the bottomhole assembly 18 may be changed as desired. Furthermore, as discussed in greater detail below, one or more of the modules 44, 46, 48 may include a fluid sampling tool configured to obtain a sample of a fluid from a subterranean formation and perform downhole fluid analysis to measure an optical property (e.g., optical density) of the sampled fluid.

In certain embodiments, the bottomhole assembly 18 may also include other types of modules. For example, as illustrated in FIG. 1, such other modules may include a power module 50, a steering module 52, and a communication module 54. In certain embodiments, the power module 50 may include a generator driven by flow of drilling mud through the drill string 16. In other embodiments, the power module 50 may also or instead include other forms of power storage or generation, such as batteries or fuel cells. In certain embodiments, the steering module 52 may include a rotary-steerable system that facilitates directional drilling of the well 14. In addition, in certain embodiments, the communication module 54 enables communication of data (e.g., data collected by the LWD module 44, the MWD module 46, and the additional module 48) between the bottomhole assembly 18 and the surface. In certain embodiments, the communication module 54 communicates via mud pulse telemetry, in which the communication module 54 uses the drilling fluid 32 in the drill string as a propagation medium for a pressure wave encoding the data to be transmitted.

In certain embodiments, the drilling system 10 may also include a monitoring and control system 56, which may include one or more computer systems that enable monitoring and control of various components of the drilling system 10. The monitoring and control system 56 may also receive data from the bottomhole assembly 18 (e.g., data from the LWD module 44, the MWD module 46, and the additional module 48) for processing and for communication to an operator, for example. While illustrated on the drill floor 30 in FIG. 1, it is noted that the monitoring and control system 56 may be positioned elsewhere, and that the monitoring and control system 56 may even be a distributed system with elements provided at different places near to or remote from the well 14.

Figure 2:
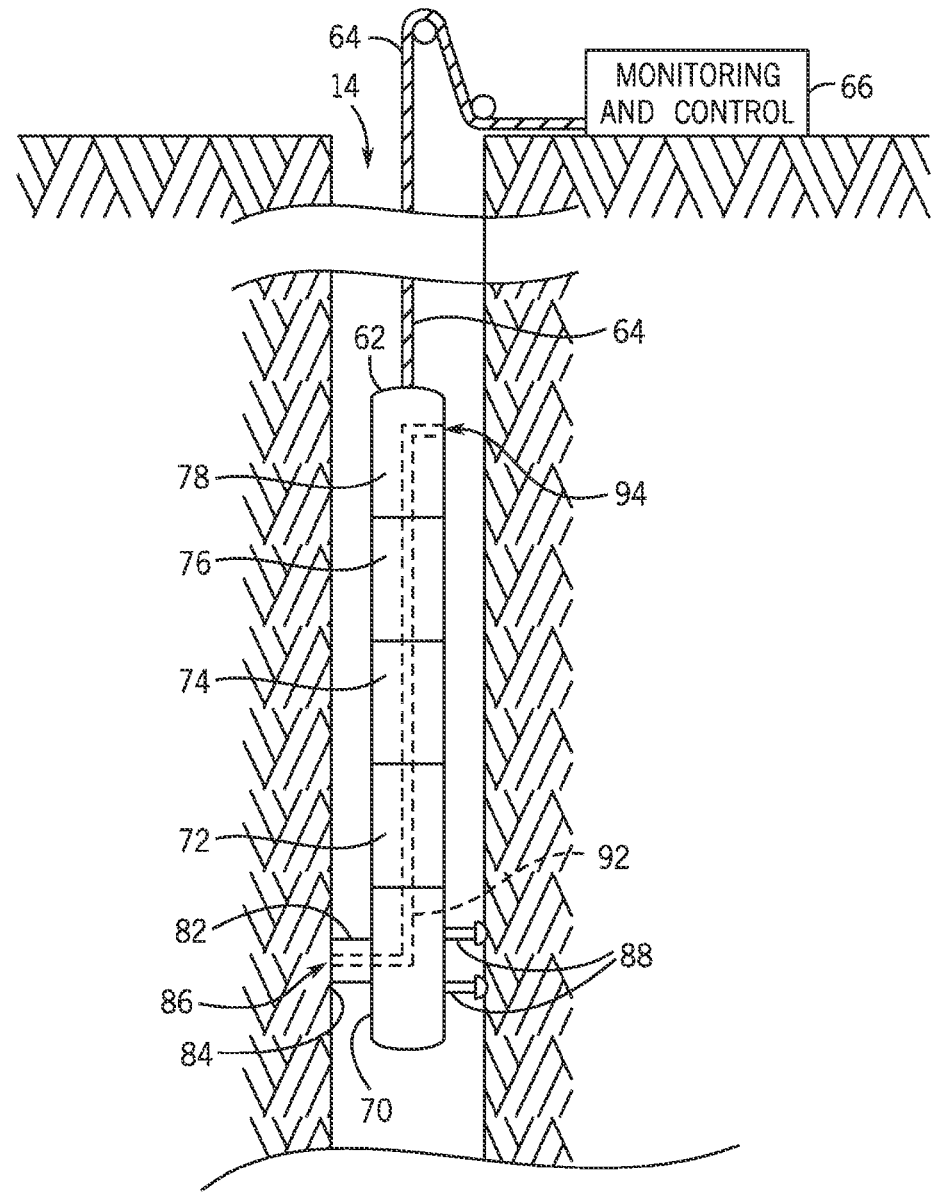
FIG. 2 illustrates a fluid sampling tool deployed within a well on a wireline, in accordance with embodiments of the present disclosure.

FIG. 2 illustrates another example of using a downhole tool for formation testing within the well 14. In this illustrated embodiment, a fluid sampling tool 62 is suspended in the well 14 on a cable 64. In certain embodiments, the cable 64 may be a wireline cable with at least one conductor that enables data transmission between the fluid sampling tool 62 and a monitoring and control system 66. The cable 64 may be raised and lowered within the well 14 in any suitable manner. For example, the cable 64 can be reeled from a drum in a service truck, which may be a logging truck having the monitoring and control system 66. In certain embodiments, the monitoring and control system 66 may control movement of the fluid sampling tool 62 within the well 14 and receive data from the fluid sampling tool 62. In a similar fashion to the monitoring and control system 56 of FIG. 1, the monitoring and control system 66 may include one or more computer systems or devices and may be a distributed computing system. In certain embodiments, the received data may be stored, communicated to an operator, or processed, for example. While the fluid sampling tool 62 is illustrated as being deployed by way of a wireline, in other embodiments, the fluid sampling tool 62 may be incorporated as one or more modules of the bottomhole assembly 18, such as the LWD module 44 or the additional module 48 illustrated in FIG. 1.

The fluid sampling tool 62 may take various forms. While it is illustrated in FIG. 2 as having a body including a probe module 70, a fluid analysis module 72, a pump module 74, a power module 76, and a fluid storage module 78, the fluid sampling tool 62 may include different modules in other embodiments. The probe module 70 may include a probe 82 that may be extended (e.g., hydraulically driven) and pressed into engagement against a wall 84 of the well 14 to draw fluid from a formation into the fluid sampling tool 62 through an intake 86. As illustrated, the probe module 70 may also include one or more setting pistons 88 that may be extended outwardly to engage the wall 84 and push the end face of the probe 82 against another portion of the wall 84. In certain embodiments, the probe 82 may include a sealing element or packer that isolates the intake 86 from the rest of the wellbore. In other embodiments, the fluid sampling tool 62 may include one or more inflatable packers that may be extended from the body of the fluid sampling tool 62 to circumferentially engage the wall 84 and isolate a region of the well 14 near the intake 86 from the rest of the wellbore. In such embodiments, the extendable probe 82 and setting pistons 88 may be omitted and the intake 86 may be provided in the body of the fluid sampling tool 62, such as in the body of a packer module housing an extendable packer.

The pump module 74 may draw the sampled formation fluid into the intake 86, through a flowline 92, and then either out into the wellbore through an outlet 94 or into a storage container (e.g., a bottle within fluid storage module 78) for transport back to the surface when the fluid sampling tool 62 is removed from the well 14. In addition, the fluid analysis module 72 may include one or more sensors for measuring properties of the sampled formation fluid, such as the optical density of the fluid, and the power module 76 may provide power to electronic components of the fluid sampling tool 62.

The drilling and wireline environments illustrated in FIGS. 1 and 2 are examples of environments in which a fluid sampling tool may be used to facilitate analysis of a downhole fluid. The presently disclosed techniques, however, may be implemented in other environments as well. For example, the fluid sampling tool 62 may be deployed in other manners, such as by a slickline, coiled tubing, or a pipe string.

Figure 3:
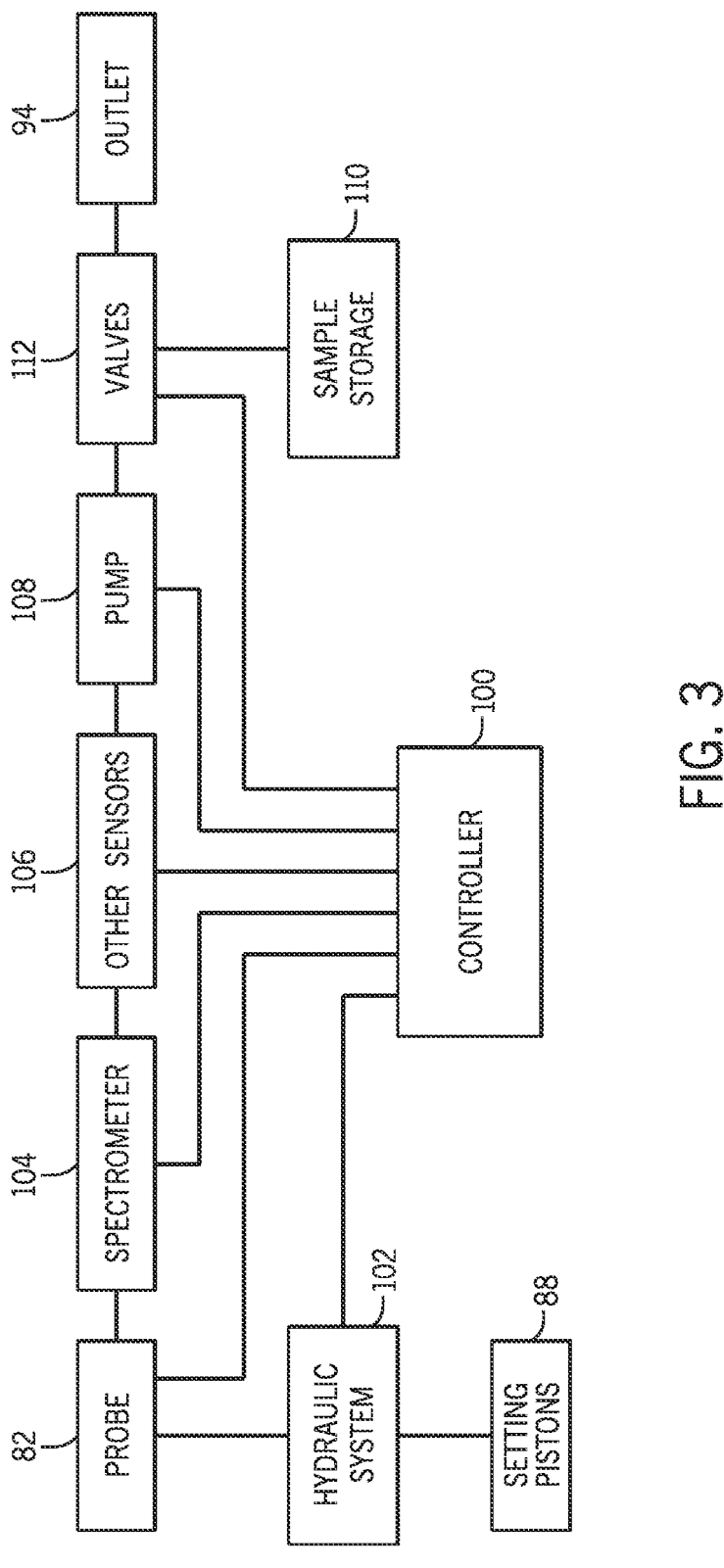
FIG. 3 is a block diagram of components of a fluid sampling tool operated by a controller, in accordance with embodiments of the present disclosure.

Additional details as to the construction and operation of the fluid sampling tool 62 may be better understood through reference to FIG. 3. As illustrated, various components for carrying out functions of the fluid sampling tool 62 may be connected to a controller 100. In certain embodiments, the controller 100 may be part of the fluid sampling tool 62.

However, in other embodiments, the controller 100 may be part of the monitoring and control systems 56, 66 disposed at the surface of the drilling system 10 illustrated in FIGS. 1 and 2. In yet other embodiments, the functionality of the controller 100 may be partially performed in the fluid sampling tool 62 and partially performed at the surface by the monitoring and control systems 56, 66. In addition, in certain embodiments, the various components may include a hydraulic system 102 connected to the probe 82 and the setting pistons 88, a spectrometer 104 for measuring fluid optical properties, one or more other sensors 106, a pump 108, and valves 112 for diverting sampled fluid into storage devices 110 rather than venting the fluid through the outlet 94.

In certain embodiments, the hydraulic system 102 may extend the probe 82 and the setting pistons 88 to facilitate sampling of a formation fluid through the wall 84 of the well 14. In addition, the hydraulic system 102 may also retract the probe 82 and the setting pistons 88 to facilitate subsequent movement of the fluid sampling tool 62 within the well. The spectrometer 104, which may be positioned within the fluid analysis module 72, collects data about optical properties of the sampled formation fluid. As described in greater detail herein, such measured optical properties may include optical densities of the sampled formation fluid at one or more wavelengths of electromagnetic radiation. In certain embodiments, other sensors 106 may be provided in the fluid sampling tool 62 (e.g., as part of the probe module 70 or the fluid analysis module 72) to take additional measurements related to the sampled fluid. In certain embodiments, these additional measurements may include pressure and temperature, density, viscosity, electrical resistivity, saturation pressure, fluorescence, and so forth. Any suitable pump 108 may be provided in the pump module 74 to enable formation fluid to be drawn into and pumped through the flowline 92. Storage devices 110 for formation fluid samples may include any suitable vessels (e.g., bottles) for retaining and transporting desired samples within the fluid sampling tool 62 to the surface. In certain embodiments, both the storage devices 110 and the valves 112 may be provided as part of the fluid storage module 78.

In the embodiment illustrated in FIG. 3, the controller 100 may facilitate operation of the fluid sampling tool 62 by controlling various components. For example, the controller 100 may direct operation (e.g., by sending command signals) of the hydraulic system 102 to extend and retract the probe 82 and the setting pistons 88 and of the pump 108 to draw formation fluid samples into and through the fluid sampling tool 62. In addition, the controller 100 may also receive data from the spectrometer 104 and the other sensors 106. This data may be stored by the controller 100 or communicated to another system (e.g., the monitoring and control systems 56, 66 described with reference to FIGS. 1 and 2) for analysis. In certain embodiments, the controller 100 may itself be capable of analyzing the data it receives from the spectrometer 104 and the other sensors 106 (e.g., while disposed within the well, without communicating the data to the monitoring and control systems 56, 66). The controller 100 may also operate the valves 112 to divert sampled fluids from the flowline 92 into the storage devices 110. In addition, as described in greater detail herein, the controller 100 may be configured to predict mass density of sampled formation fluids based on optical absorbance of the sampled formation fluids at various wavelengths in the near infrared spectrum, and to predict percentage levels of gases without an optical signature in the near infrared spectrum.

Figure 4:
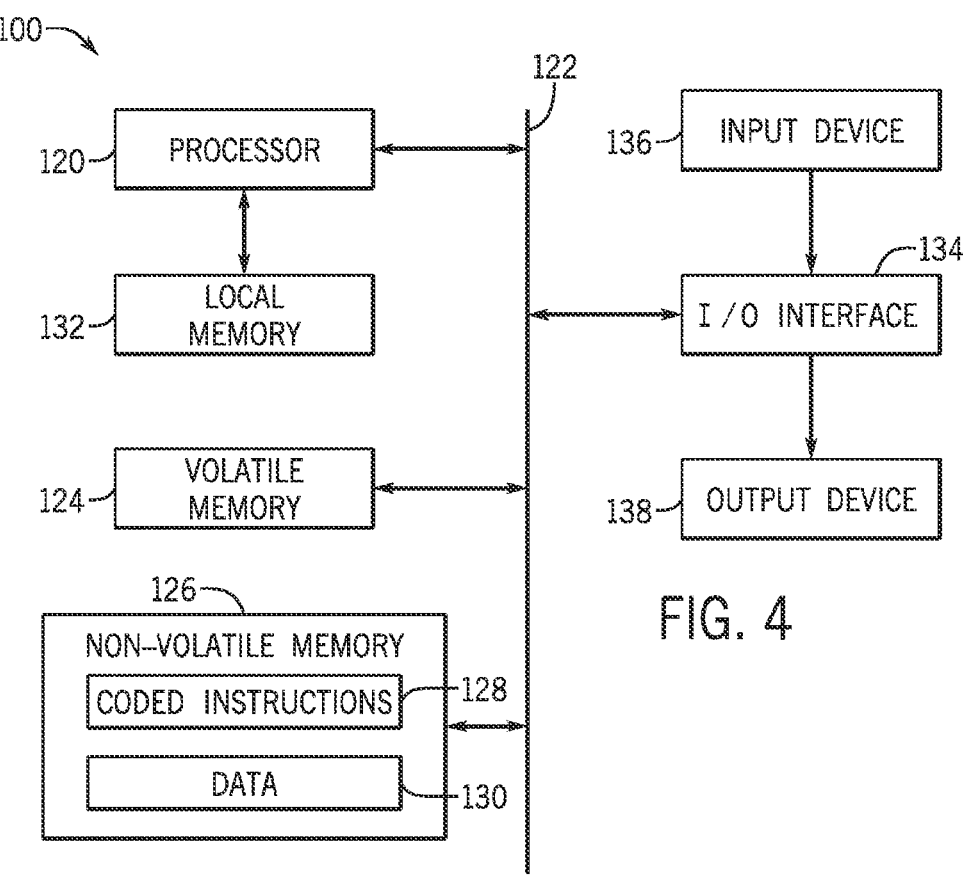
FIG. 4 is a block diagram of components of the controller illustrated in FIG. 3, in accordance with embodiments of the present disclosure.

In certain embodiments, the controller 100 may be a processor-based system, an example of which is illustrated in FIG. 4. In the illustrated embodiment, the controller 100 may include at least one processor 120 connected, by a bus 122, to volatile memory 124 (e.g., random-access memory) and non-volatile memory 126 (e.g., flash memory and a read-only memory (ROM)). Coded application instructions 128 (e.g., software that may be executed by the processor 120 to enable the control and analysis functionality described herein) and data 130 are stored in the non-volatile memory 126. For example, in certain embodiments, the application instructions 128 may be stored in a ROM and the data may be stored in a flash memory. The coded instructions 128 and the data 130 may also be loaded into the volatile memory 124 (or in a local memory 132 of the at least one processor 120) as desired, such as to reduce latency and increase operating efficiency of the controller 100.

In certain embodiments, an interface 134 of the controller 100 may enable communication between the at least one processor 120 and various input devices 136 and output devices 138. The interface 134 may include any suitable device that enables such communication, such as a modem or a serial port. In certain embodiments, the input devices 136 may include one or more sensing components of the fluid sampling tool 62 (e.g., the spectrometer 104) and the output devices 138 may include displays, printers, and storage devices that allow output of data received or generated by the controller 100. In certain embodiments, the input devices 136 and output devices 138 may be provided as part of the controller 100 although, in other embodiments, such devices may be separately provided.

In certain embodiments, the controller 100 may be provided as part of the monitoring and control systems 56, 66 outside of a well 14 to enable downhole fluid analysis of samples obtained by the fluid sampling tool 62. In such embodiments, data collected by the fluid sampling tool 62 may be transmitted from the well 14 to the surface for analysis by the controller 100. In other embodiments, the controller 100 may instead be provided within a downhole tool in the well 14, such as within the fluid sampling tool 62 or in another component of the bottomhole assembly 18 to enable downhole fluid analysis to be performed within the well 14. Furthermore, in certain embodiments, the controller 100 may be a distributed system with some components located in a downhole tool and others provided elsewhere (e.g., at the surface of the wellsite). Whether provided within or outside the well 14, the controller 100 may receive data collected by the sensors within the fluid sampling tool 62 and process this data to determine one or more characteristics of the sampled fluid. Examples of such characteristics include fluid type, gas-to-oil ratio, carbon dioxide content, water content, contamination, and so forth.

Figure 5:
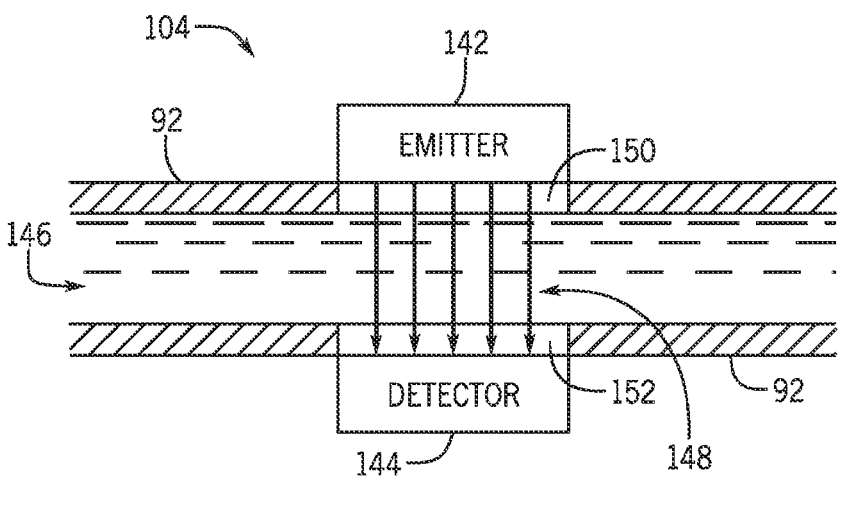
FIG. 5 illustrates a spectrometer positioned about a flowline to enable measurement of an optical property of a fluid within the flowline, in accordance with embodiments of the present disclosure.

Some of the data collected by the fluid sampling tool 62 relates to optical properties (e.g., optical densities) of a sampled fluid measured by the spectrometer 104. To facilitate measurements, in certain embodiments, the spectrometer 104 may be disposed about the flowline 92 of the fluid sampling tool 62 as illustrated in FIG. 5. In certain embodiments, the spectrometer 104 may include an emitter 142 of electromagnetic radiation, such as a light source, and a detector 144 disposed about the flowline 92 in the fluid sampling tool 62. A light source provided as the emitter 142 may be any suitable light-emitting device, such as one or more light-emitting diodes or incandescent lamps. As used herein, the term "visible light" is intended to mean electromagnetic radiation within the visible spectrum, and the shorter term "light" is intended to include not just electromagnetic radiation within the visible spectrum, but also infrared and ultraviolet radiation.

In operation, a sampled formation fluid 146 within the flowline 92 may be irradiated with electromagnetic radiation 148 (e.g., light) from the emitter 142. The electromagnetic radiation 148 includes radiation of any desired wavelengths within the electromagnetic spectrum. In certain embodiments, the electromagnetic radiation 148 has a continuous spectrum within one or both of the visible range and the near-infrared range of the electromagnetic spectrum, and the detector 144 may filter or diffract the received electromagnetic radiation 148. In certain embodiments, the detector 144 may include a plurality of detectors, each assigned to separately measure light of a different wavelength. As illustrated in FIG. 5, the flowline 92 may include windows 150, 152 that isolate the emitter 142 and the detector 144 from the sampled formation fluid 146 while still permitting the electromagnetic radiation 148 to be transmitted and measured. As will be appreciated, a portion of the electromagnetic radiation 148 may be absorbed by the sampled formation fluid 146, and the extent of such absorption may vary for different wavelengths and sampled formation fluids 146. The optical density of the sampled formation fluid 146 at one or more wavelengths may be determined based on data from the spectrometer 104 by comparing the amount of radiation emitted by the emitter 142 and the amount of that radiation received at the detector 144. It will be appreciated that the optical density (also referred to as the absorbance) of a sampled formation fluid 146 at a given wavelength may be calculated as the base-ten logarithm of the ratio of electromagnetic radiation incident on the sampled formation fluid 146 to that transmitted through the sampled formation fluid 146 for the given wavelength.

In certain embodiments, the spectrometer 104 may include any suitable number of measurement channels for detecting different wavelengths, and may include a filter-array spectrometer or a grating spectrometer. For example, in certain embodiments, the spectrometer 104 may be a filter-array absorption spectrometer having sixteen measurement channels. In other embodiments, the spectrometer 104 may have ten channels or twenty channels and may be provided as a filter-array spectrometer or a grating spectrometer.

As described above, the embodiments presented herein include systems and methods for predicting the mass density of sampled formation fluids 146 captured by the fluid sampling tool 62. In particular, the controller 100 of the fluid sampling tool 62 may be configured to analyze optical absorbance at various wavelengths, as measured by the spectrometer 104 of the fluid sampling tool 62. In certain embodiments, these absorbances may be used by the controller 100 in combination with a physics-based model, a statistical model, a machine learning model, or artificial neural networks to predict the composition of the sampled formation fluids 146.

Figure 7:
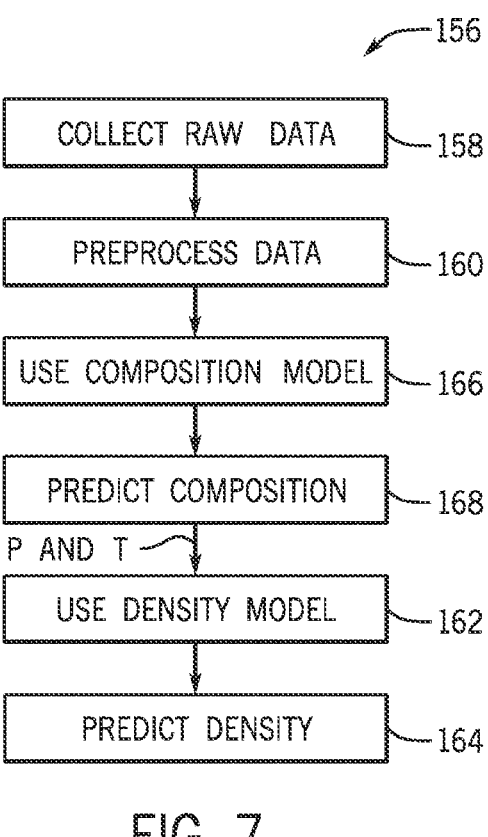
FIG. 7 is a flow diagram of a second method to predict mass density of a sample formation fluid, in accordance with embodiments of the present disclosure.

FIGS. 6A, 6B, and 7 illustrate a first method 154 (with two alternate routes) and a second method 156 to predict the mass density from optical data, as described in greater detail herein. In certain embodiments, the first method 154 goes directly from the optical data to a predicted mass density and may be done using either a statistical model, machine learning or artificial neural networks. In particular, as illustrated in FIG. 6A, the first method 154 includes collecting raw optical data relating to a sampled formation fluid 146 (step 158), preprocessing the collected raw optical data (step 160A), then using a density model (step 162) to predict the mass density of the sampled formation fluid 146 (step 164)

based at least in part on the preprocessed optical data. As described in greater detail below, in an alternative embodiment, the first method 154 includes collecting raw optical data relating to a sampled formation fluid 146 (step 158), preprocessing the collected raw optical data (step 160A) as well as normalizing the preprocessed optical data (step 160B), then using a density model (step 162) to predict the mass density of the sampled formation fluid 146 (step 164) based at least in part on the preprocessed optical data. In either route illustrated in FIGS. 6A and 6B, the density models may include statistical models, machine learning models, or artificial neural networks. In addition, in certain embodiments, the density models may be trained with data stored in a database, wherein the training data includes optical absorption data, pressure data, temperature data, and density data.

In contrast, the second method 156 first predicts a composition and then uses this composition to predict a mass density. In particular, as illustrated in FIG. 7, the second method 156 includes collecting raw optical data relating to a sampled formation fluid 146 (step 158), preprocessing the collected raw optical data (step 160), then using a compositional model (step 166) to predict compositions of individual components of the sample fluid (step 168) based at least in part on the preprocessed optical data. Then, based on the predicted compositions of individual components of the sampled formation fluid 146, the method 156 includes using a density model (step 162) to predict the mass density of the sampled formation fluid 146 (step 164) based at least in part on the predicted compositions of individual components of the fluid. The compositional model may also include a physics-based model, a statistical model, a machine learning model, or artificial neural networks. In addition, in certain embodiments, the density model may also access a relatively large database that includes optical data, density data, and compositional data.

In more detail, again, the first method 154 starts with raw optical data. To offset scattering, the optical absorbance values may be zeroed at a wavelength of 1600 nanometers (e.g., as part of the preprocessing step 160A of the raw optical data). Next, in the route illustrated in FIG. 6A, a first density model may be used to predict the mass density using the optical data with or without pressure (P) and temperature (T). Alternatively, in certain embodiments where no gases without an optical signature are expected, a second density model may be used to predict the mass density based on normalized data and P and T. In this alternative route illustrated in FIG. 6B, the data may undergo a second preprocessing step 160B. In particular, for example, after zeroing at 1600 nm in the first preprocessing step 160A, the data may be normalized to one of the hydrocarbon channels (e.g., between 1600 nm and 1800 nm) in the second preprocessing step 160B. In certain embodiments, if the predictions of both routes illustrated in FIGS. 6A and 6B are relatively close together (e.g., less than 2% of each other, less than 1% of each other, less than 0.5% of each other, or even closer), the mass density is presumed to be correct. In certain embodiments, the predicted value from either route illustrated in FIG. 6A or 6B (or a weighted average of both routes) may be used as the final prediction. In either route illustrated in FIGS. 6A and 6B, the density models may include statistical models, machine learning models, or artificial neural networks. In addition, in certain embodiments, the density models may be trained with data stored in a database, wherein the training data includes optical absorption data, pressure data, temperature data, and density data.

One example of a statistical model may be developed using a direct partial least squares (PLS) method using the optical absorbance of all wavelengths in the near infrared region where the hydrocarbons absorb, in combination with independently measured densities, to train the PLS system. In certain embodiments, the PLS system using a mean center preprocessing step may provide the best results. However, it will be appreciated that such data preprocessing may be omitted or other preprocessing steps may be used. Furthermore, in other embodiments, other statistical methods such as principal component analysis (PCA) may be used to enable the prediction of the mass density as well.

Figure 8:
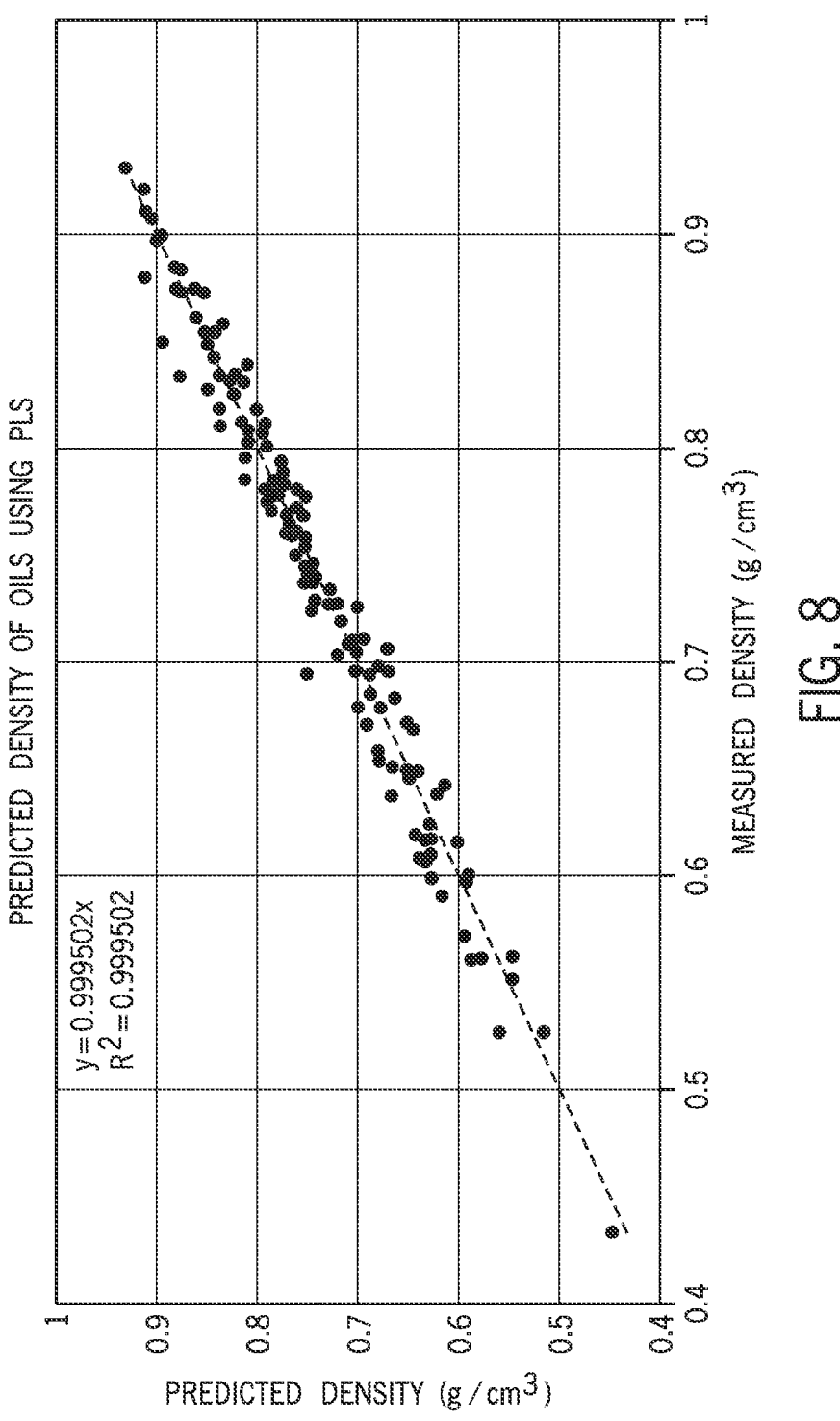
FIG. 8 is a graph of predicted mass density versus measured mass density of oils using a partial least squares (PLS) model with six latent variables, in accordance with embodiments of the present disclosure.
Figure 9:
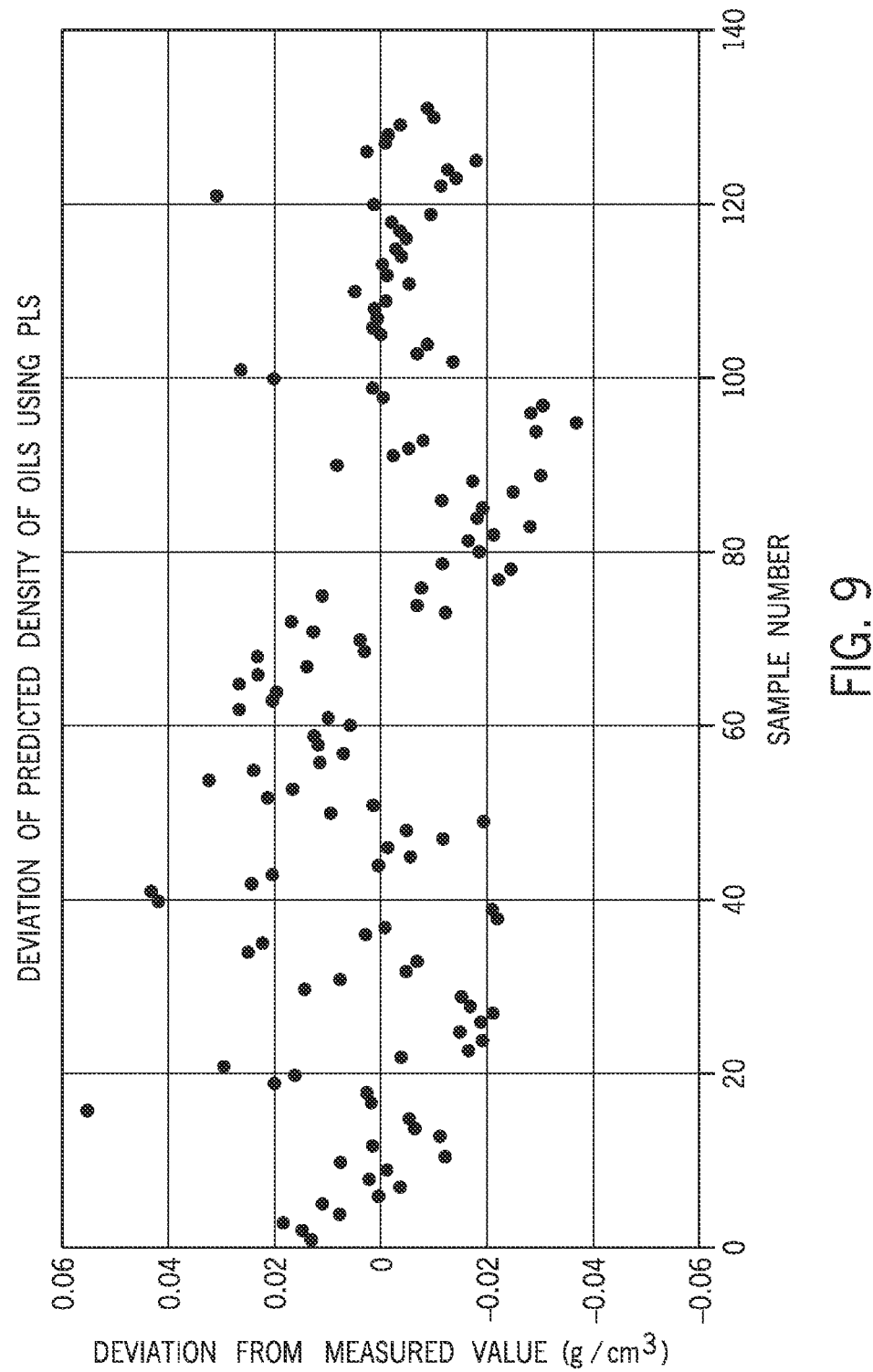
FIG. 9 is a graph of deviations of predicted mass density from measured mass density for oils (e.g., of the data in FIG. 8), in accordance with embodiments of the present disclosure.

FIG. 8 illustrates the relation between the measured density and the predicted mass density for oils using a mean center preprocessing step for both the x and y blocks (e.g., for fluids that are known to have no or small amounts of gases that have no optical signature at the wavelengths used for this measurement; therefore only the route illustrated in FIG. 6A, including P and T, is used). This set of data consists of 19 oils at various pressures and temperatures for a total of 131 data points. The data illustrates very close correlation (e.g., $R^2$ of 0.999502), which can also be seen in FIG. 9, where the deviation between predicted and measured mass density is plotted for all 131 measurement points. Almost all points are within 0.04 $g/cm^3$ and most points are even within 0.02 $g/cm^3$ from the lab measurements.

Figure 10:
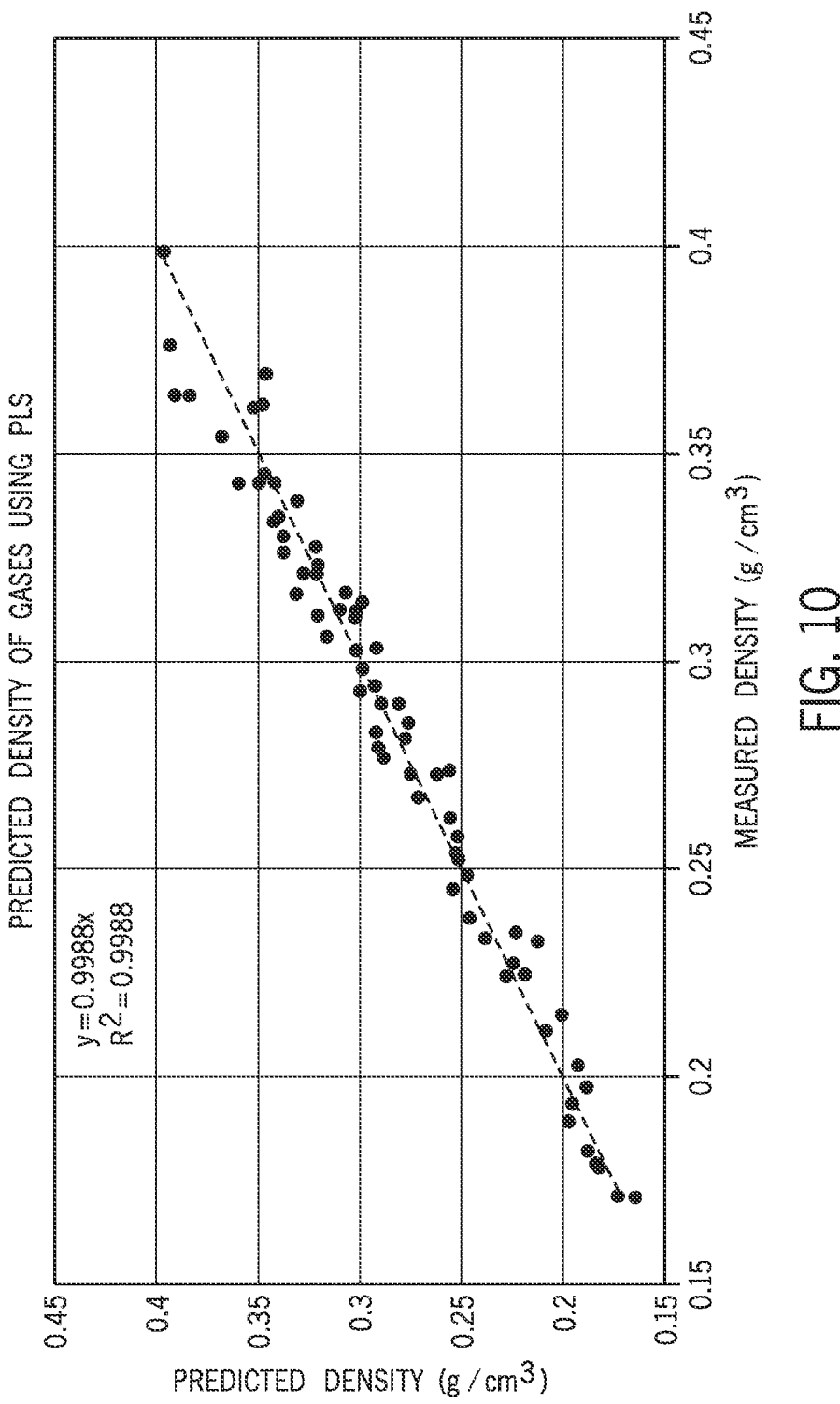
FIG. 10 is a graph of predicted mass density versus measured mass density of gases using a PLS model with five latent variables, in accordance with embodiments of the present disclosure.

As another test, a set of six gases at various pressures and temperatures for a total of 71 data points illustrated even better results, as can be seen in FIG. 10. In this test, no preprocessing steps were performed, and five latent variables were used. The correlation is again very close (e.g., $R^2$ of 0.9988), and all points are within 0.03 g/cm3 with the majority within 0.01 $g/cm^3$ from the lab measurements.

Figure 11:
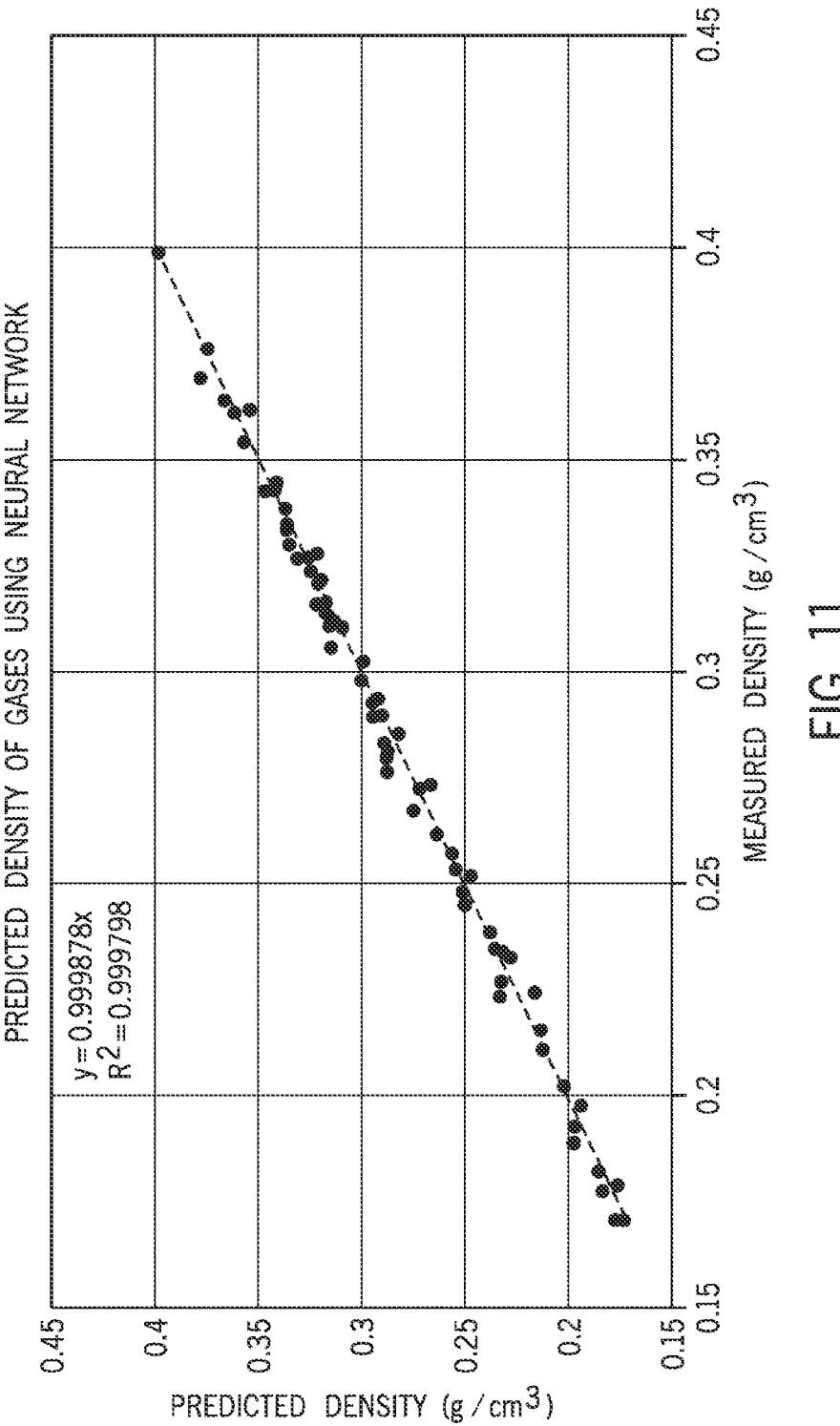
FIG. 11 is a graph of predicted mass density versus measured mass density of gases using a neural network with two nodes, in accordance with embodiments of the present disclosure.
Figure 12:
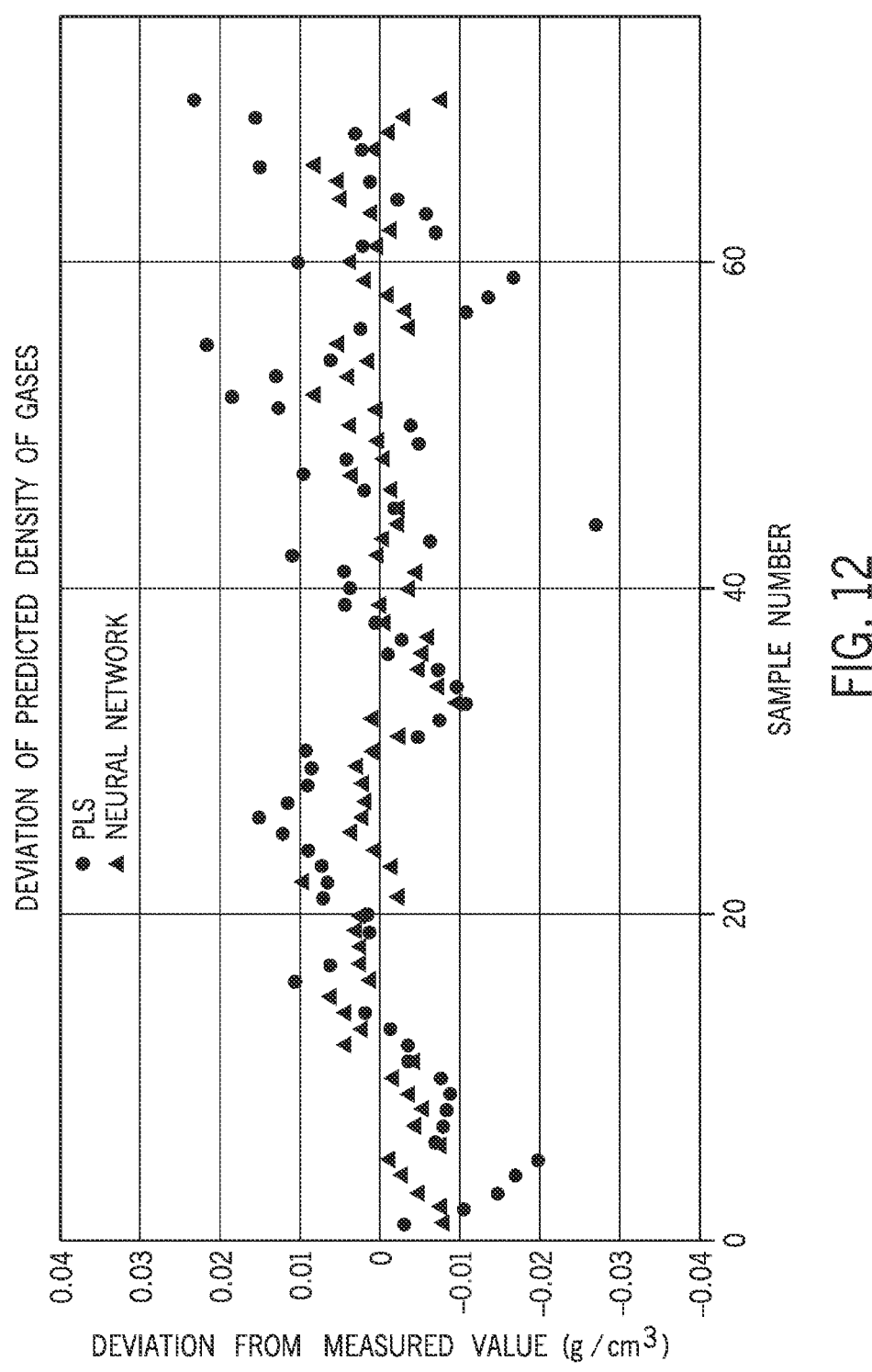
FIG. 12 is a graph of deviations of predicted mass density from measured mass density for gases (e.g., of the data in FIG. 11), in accordance with embodiments of the present disclosure.

In certain embodiments, more advanced techniques like artificial neural networks or machine learning techniques like gradient boosting may be used to predict the mass density. The quality of the predictions of these methods is strongly dependent on the quality and quantity of the reference data. In this example, an artificial neural network with only two nodes was used. The same data set of six gases at various pressures and densities for a total of 71 data points was used in the mass density predictions. As illustrated in FIG. 11, the predictions exhibit very close agreement with the true values (e.g., $R^2$ of 0.999798). It is clear from these results that neural networks may be used to determine the mass density. FIG. 12 illustrates the deviation from the lab measurements for both the PLS method and the neural network method. As illustrated in FIG. 12, all values predicted with the neural network are within 0.01 $g/cm^3$.

Returning to FIG. 7, the second method 156 also starts with raw optical data. Preprocessing steps to offset scattering, pressure, and temperature are performed and then a composition model may be used to predict compositions (e.g., of individual components of the sampled formation fluid 146) in either weight percentages or mole percentages. In certain embodiments, the composition model may be a physics-based model, a statistical model, a machine learning model, or artificial neural networks. The composition model may result in predicted weight fractions for $C_1$, $C_2$, $C_3$, $C_4$, $C_5$, $CO_2$ and $C_{6+}$ (e.g., with $C_{6+}$ being all the components of the sampled formation fluid 146 with six or more carbon atoms). Then, a density model may use the predicted compositions, pressure, and temperature of the sampled formation fluid 146 to predict the mass density. In certain embodiments, the density model may be trained with a database including compositions, pressure, temperature, and density data. In certain embodiments, the density model may be a physics-based model, a statistical model, a machine learning model, or an artificial neural network.

In certain embodiments, the obtained mass density predictions determined by either method 154, 156 may be used to validate the mass density measurements obtained by the fluid sampling tool 62. In other embodiments, the obtained mass density predictions for both methods 154, 156 may be compared to each other for validation. Furthermore, in certain embodiments, the mass density predictions obtained from the first method 154 and/or the second method 156 may be used by the controller 100 and/or the monitoring and control systems 56, 66 to adjust operating parameters of the drilling system 10.

As described above, the embodiments presented herein also include systems and methods for predicting percentage levels of gases in sampled formation fluids 146 not observed by optical measurements of the spectrometer 104 of the fluid sampling tool 62 using one or three different methods: (1) direct mass density measurement in the fluid sampling tool 62; (2) predicted hydrocarbon and carbon dioxide compositions in combination with pressure and temperature in an equation of state (EOS) to calculate an expected mass density; (3) direct prediction of the mass density using a PLS algorithm in combination with optical measurements (e.g., as obtained using the route described above with respect to FIG. 6A).

Figure 13A:
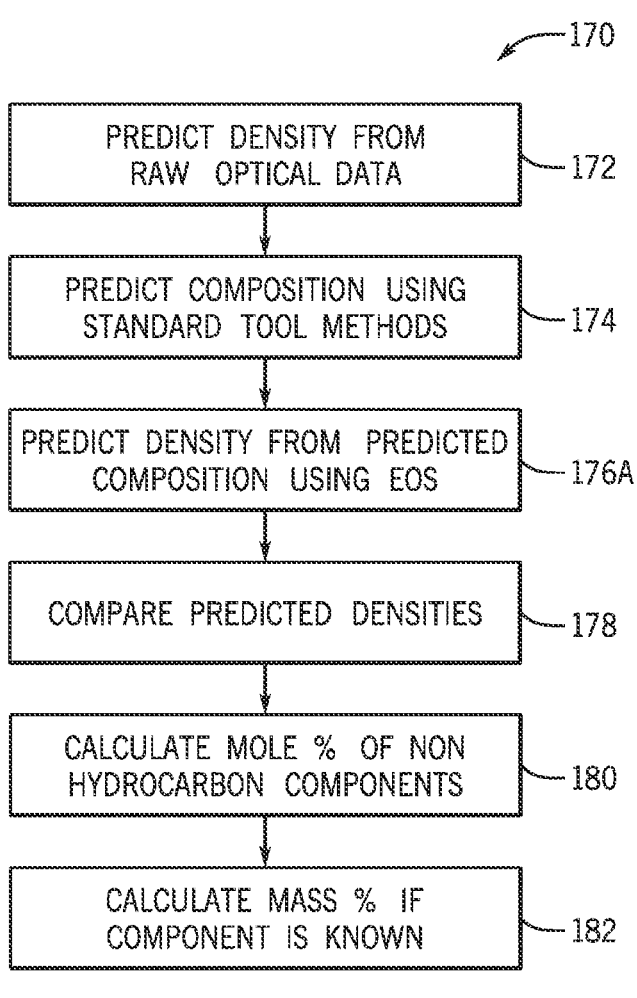
FIGS. 13A and 13B are flow diagrams of a density-based method to predict percentage levels of gases in sampled formation fluids, in accordance with embodiments of the present disclosure.
Figure 13B:
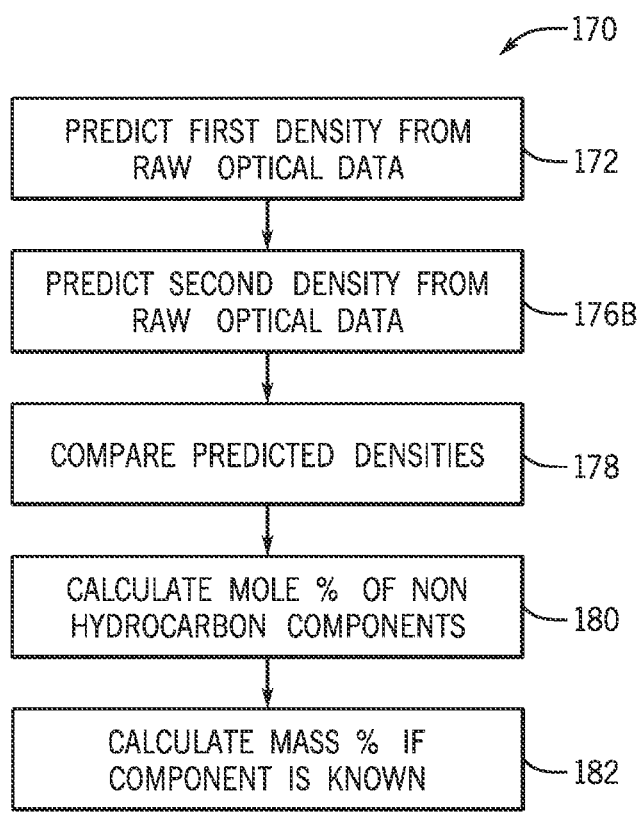

FIGS. 13A and 13B are flow diagrams of a density-based method 170 to predict percentage levels of gases in sampled formation fluids 146. In a first example, a first gas is considered that contains only detectable hydrocarbons and carbon dioxide. In step 172 of the method 170, the mass density of the first gas (i.e., the optics-based mass density) may be predicted using raw optical data that is only set to zero at a wavelength that has no hydrocarbon and carbon dioxide based optical absorption using a PLS algorithm (e.g., as obtained using the route described above with respect to FIG. 6A). In step 174 of the method 170, compositions of individual components of the first gas are calculated (e.g., using traditional tool methods). In certain embodiments, this step 174 starts with a normalization on one of the dominant hydrocarbon peaks. The normalization makes the measurement independent of temperature, pressure, and the presence of gases without optical signatures, among other things. In step 176A of the method 170, the predicted compositions (e.g., from step 174) combined with the pressure and temperature are used in an equation of state (EOS) model to predict the mass density of the first gas (i.e., the EOS-based mass density). Step 178 of the method 170 compares the optics-based mass density (e.g., from step 172) to the EOS-based mass density (from step 176A). These two densities should be the same or relatively close together, thus indicating that there are only hydrocarbon and carbon dioxide gases present. In certain embodiments, in a final verification, the measured mass density may be compared to the predicted densities and should show a similar mass density, thus confirming that only hydrocarbon and carbon dioxide gases are present. In general, the densities not matching (e.g., within a certain threshold) indicate that non-hydrocarbon components are present within the first gas. Indeed, the percentage difference between the densities may indicate an amount of non-hydrocarbon components that are present within the first gas.

In a second example, a second gas is considered that consists of the first gas (e.g., from the first example of the preceding paragraph) with 10% volume of a lighter gas without an optical signature (e.g., hydrogen or helium). In step 172 of the method 170, the optics-based mass density may be predicted based on the raw data that are only set to zero at a wavelength that has no hydrocarbon and carbon dioxide based optical absorption using a PLS algorithm (e.g., as obtained using the route described above with respect to FIG. 6A). Since the volume of hydrocarbons and carbon dioxide is only approximately 90% for the second gas, the optical density at each wavelength is reduced to approximately 90% of the value in the first example of the preceding paragraph. Therefore, the predicted optics-based mass density will also be only approximately 90% of the predicted mass density for the first gas (e.g., from the first example of the preceding paragraph). In step 174 of the method 170, compositions of individual components of the second gas may be calculated (e.g., using traditional tool methods). In certain embodiments, this step 174 starts with a normalization on one of the dominant hydrocarbon peaks. The normalization makes the measurement independent of temperature, pressure, and the presence of gases without optical signatures, among other things. Therefore, the predicted compositions of individual components of the second gas are the same as for the first gas and, thus, the EOS-based mass density (e.g., as predicted in step 176A) should be the same as well. Step 178 of the method 170 compares the optics-based mass density (e.g., from step 172) to the EOS-based mass density (from step 176A). These densities should be about 10% different, thus indicating that there is about 10% volume of a gas without an optical signature. In step 180 of the method 170, the 10% volume fraction may be converted to a 10% mole fraction, assuming an ideal gas. The ideal gas law is assumed for simplicity, although it is worth noting that similar behavior will result from the use of more accurate non-ideal gas equations or an appropriately selected full equation of state. If it is known which gas without an optical signature is present, the mole fraction may be converted to a mass fraction in step 182 of the method 170. The mass density of the second gas that is measured by the fluid sampling tool 62 should be in a range of approximately 4-9% lower relative to the first gas (e.g., specifically, approximately 4% lower for helium in pure methane and more than 9% lower for hydrogen in a gas mixture with an average molecular weight above 20 daltons).

In a third example, a third gas is considered that consists of the first gas (e.g., from the first example of two paragraphs ago) with 10% volume of a heavier gas without an optical signature (e.g., hydrogen sulfide or nitrogen). In step 172 of the method 170, the optics-based mass density may be predicted based on the raw data that are only set to zero at a wavelength that has no hydrocarbon and carbon dioxide based optical absorption using a PLS algorithm (e.g., as obtained using the route described above with respect to FIG. 6A). Since the volume of hydrocarbons and carbon dioxide is only approximately 90% for the second gas, the optical density is reduced to approximately 90% of the value in the first example of two paragraphs ago. Therefore, the predicted optics-based mass density will also be only approximately 90% of the predicted mass density for the first gas (e.g., from the first example of two paragraphs ago). In step 174 of the method 170, compositions of individual components of the second gas may be calculated (e.g., using traditional tool methods). In certain embodiments, this step 174 starts with a normalization on one of the dominant hydrocarbon peaks. The normalization makes the measurement independent of temperature, pressure, and the presence of gases without optical signatures, among other things. Therefore, the predicted compositions of individual components of the third gas are the same as for the first gas and, thus, the EOS-based mass density (e.g., as predicted in step 176A) should be the same as well. Step 178 of the method 170 compares the optics-based mass density (e.g., from step 172) to the EOS-based mass density (from step 176A). These densities should be about 10% different, thus indicating that there is about 10% volume of a gas without an optical signature. In step 180 of the method 170, the 10% volume fraction may be converted to a 10% mole fraction, assuming an ideal gas. The ideal gas law is assumed for simplicity, although it is worth noting that similar behavior will result from the use of more accurate non-ideal gas equations or an appropriately selected full equation of state. If it is known which gas without an optical signature is present, the mole fraction may be converted to a mass fraction in step 182 of the method 170. The mass density of the third gas that is measured by the fluid sampling tool 62 should be in a range of approximately 4-10% higher relative to the first gas. The exact mass density values will depend on the composition of the first gas mixture and which heavy component is present in the third gas mixture.

In all three of the examples described above, the mass density may be predicted using an equation of state. This method 170 predicts mass density based on an assumption that the gases are 100% hydrocarbons and carbon dioxide. However, other methods are possible as well including, but not limited to, PLS-based methods, non-ideal gas law, and so forth. For example, in certain embodiments, the route illustrated in FIG. 6B may be utilized instead of using an equation of state. In particular, another method to predict gases not observed by optical methods may be implemented. For example, when the two routes described above with reference to FIGS. 6A and 6B are used to predict densities, and the difference between the two densities is more than a certain amount (e.g., greater than 0.5%, greater than 1.0%, greater than 2.0%, or even greater), the difference may be indicative to the presence of gases not measured by the optics. In such instances, the two densities predicted by the routes described above with reference to FIGS. 6A and 6B may be used in combination.

For example, FIG. 13B illustrates an alternative density-based method 170 to predict percentage levels of gases in sampled formation fluids 146. In step 172 of the alternative method 170 illustrated in FIG. 13B, a first mass density of the gas (i.e., a first optics-based mass density) may be predicted using raw optical data that is only set to zero at a wavelength that has no hydrocarbon and carbon dioxide based optical absorption using a PLS algorithm (e.g., as obtained using the route described above with respect to FIG. 6A). In step 176B of the alternative method 170 illustrated in FIG. 13B, instead of using an EOS model to predict an EOS-based mass density, a second mass density of the gas (i.e., a second optics-based mass density) may be predicted using raw optical data using the route described above with respect to FIG. 6B. Then, steps 178, 180, and 182 of the alternative method 170 illustrated in FIG. 13B may be similar to those described with reference to FIG. 13A, with the sole difference being that the densities compared in step 178 are the first and second optical-based mass densities predicted using the two routes described above with reference to FIGS. 6A and 6B.

Figure 14:
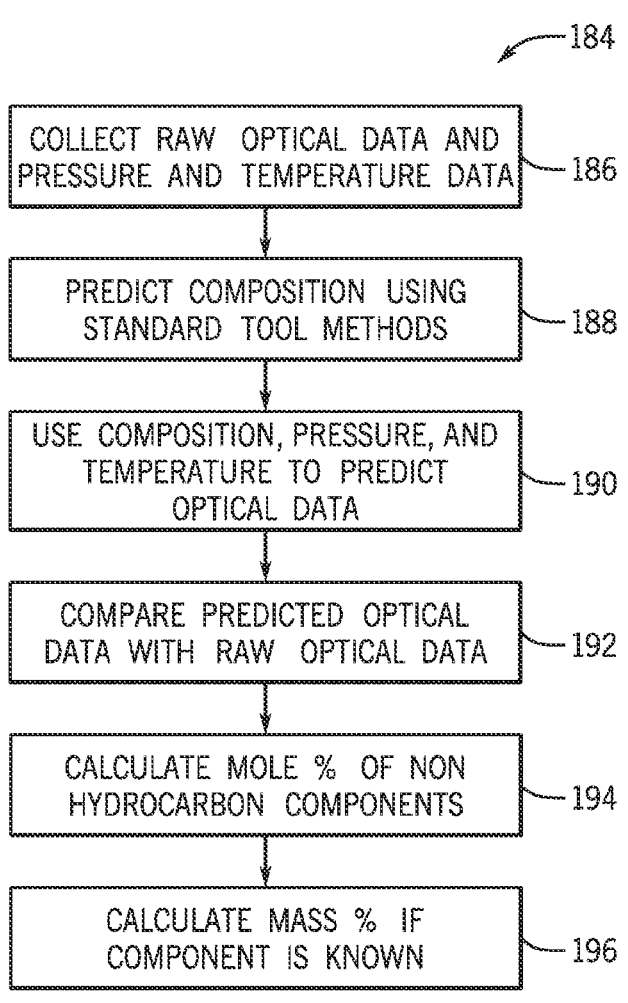
FIG. 14 is a flow diagram of an optics-based method to predict percentage levels of gases in sampled formation fluids, in accordance with embodiments of the present disclosure.

FIG. 14 is a flow diagram of an optics-based method 184 to predict percentage levels of gases in sampled formation fluids 146. The compositions predicted by the fluid sampling tool 62 include weight percentages of $C_1$, $C_2$, $C_3$, $C_4$, $C_5$, $C_{6+}$, and carbon dioxide. The compositional predictions, combined with pressure and temperature information, may then be used to predict the optical absorption.

In a first example, a first gas is considered that contains only detectable hydrocarbons and carbon dioxide. This method 184 starts with collecting the raw optical data and pressure and temperature information (step 186). In step 188 of the method 184, compositions of individual components of the first gas may be calculated (e.g., using traditional tool methods). The prediction algorithm starts with setting the spectrum to zero at a wavelength that has no hydrocarbon and carbon dioxide based optical absorption followed by a normalization on one of the dominant hydrocarbon peaks. The normalization makes the measurement independent of temperature, pressure, and the presence of gases without optical signatures, among other things. In step 190 of the method 184, the predicted compositions, the pressure, and the temperature may be used to predict the optical data. In step 192 of the method 184, the predicted optical data may be compared to the raw optical data (e.g., as obtained using the spectrometer 104 of the fluid sampling tool 62). Since there are no undetectable gases in the first gas, the predicted optical data and the measured optical data should be the same or very close together.

In a second example, a second gas is considered that consists of the first gas (e.g., from the first example of the preceding paragraph) with 10% volume of a gas without an optical signature. Since the volume of hydrocarbons and carbon dioxide is only 90% for the second gas, the optical density at each wavelength is reduced to 90% of the value in the first example of the preceding paragraph. In step 188, the normalization will result in the same normalized spectrum and predicted compositions and, thus, predicted optical data (e.g., as predicted in step 190). In step 192 of the method 184, a comparison between the predicted optical spectrum and the measured optical spectrum should be approximately 10%, thus indicating the presence of 10% undetectable gas. In step 194 of the method 184, the 10% volume fraction may be converted to a 10% mole fraction, assuming an ideal gas. The ideal gas law is assumed for simplicity, although it is worth noting that similar behavior will result from the use of more accurate non-ideal gas equations or an appropriately selected full equation of state. If it is known which gas without an optical signature is present, the mole fraction may be converted to a mass fraction in step 196 of the method 184.

In certain embodiments, if methods 170, 184 are both performed, as comparison may be made between the predicted concentrations of the unknown gas. Since both methods 170, 184 are independent, the accuracy of the measurements should be improved by such comparison. In certain embodiments, the final answer may be an average of the two values determined by the methods 170, 184, or eventually if it is determined that there is a bias in one or both of the methods 170, 184, such bias may become a weighted average of the two methods 170, 184.

Figure 15:
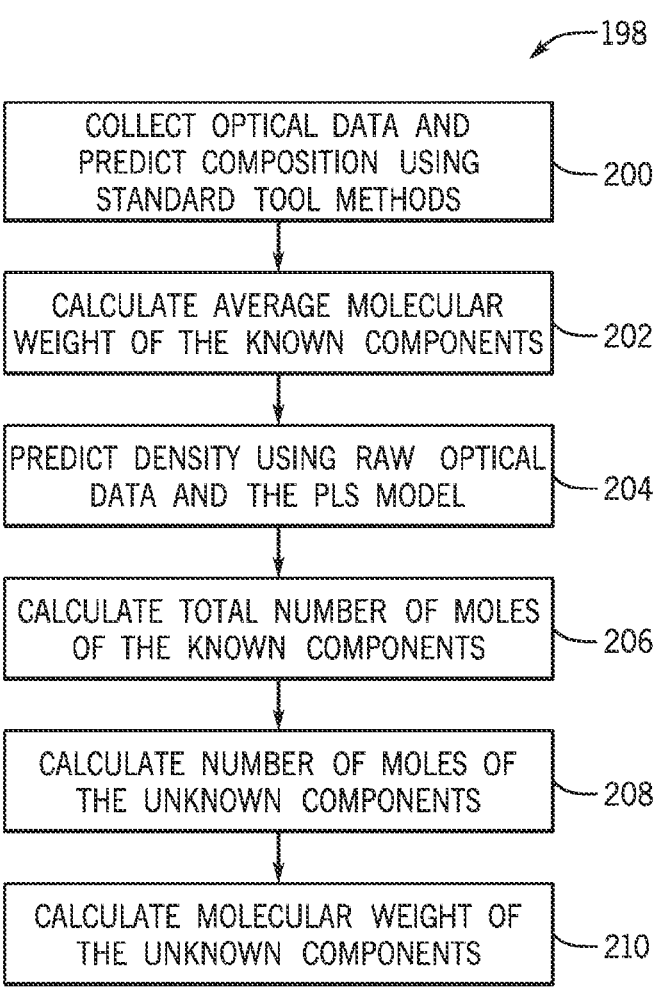
FIG. 15 is a flow diagram of a method for prediction of the molar mass of an inorganic gas.

The methods 170, 184 predict the presence of an undetectable gas, but are unable to identify the gas. However, identification of the unknown gas may be possible if the predictions of the compositions and the mass density and the mass density measurement are accurate and there is an indication of the molar weight of $C_{6+}$. FIG. 15 is a flow diagram of a method 198 for prediction of the molar mass of an inorganic gas. In step 200 of the method 198, the composition of the detectable components may be predicted and converted to mole % using traditional tool methods. In step 202 of the method 198, the average molecular weight may be calculated using an estimation of the $C_{6+}$ weight.

$$\frac{\sum \text{mol. } \% * mw}{100} = \text{average mol weight}$$

In step 204 of the method 198, the mass density of the gas may be predicted using a PLS model on raw optical data. This is a mass density solely attributed to the hydrocarbon components and carbon dioxide in the gas. The number of moles of known components of the gas may thus be calculated by dividing this predicted mass density by the average molecular weight (step 206 of the method 198). Since the mole fraction may be known from either of the methods 170, 184, the number of moles of the undetectable gas may be calculated (step 208 of the method 198):

$$\frac{\text{\# moles known } comp \text{ (step 206)}}{\text{mole } \% \text{ known } comp} * \text{mole } \% \text{ unknown } comp =$$

$$\text{\# moles unknown } comp$$

In the final step 210 of the method 198, the difference between the measured mass density and the predicted mass density may be attributed to the unknown component of the gas and divided by the number of moles to obtain the molecular weight of the unknown component of the gas.

$$\frac{\text{measured density} - \text{predict density (step 202)}}{\text{\# moles unknown } comp} =$$

$$\text{mol weight inknown } comp$$

The molecular weight may then be used to identify the unknown component or, in the case of two undetectable but known components, to determine a ratio between these components.

Aspects of the claims are disclosed. The recitation of the features of the claims should not be considered to limit the disclosure. In one example embodiment of the disclosure, a fluid sampling system is provided. The fluid sampling system comprises a fluid sampling tool comprising: a probe configured to draw a fluid from a formation within which the fluid sampling tool is disposed during an oil and gas well operation; and a spectrometer configured to detect raw data relating to optical properties of the fluid, wherein the raw data relating to the optical properties of the fluid comprises optical absorbance at a plurality of wavelengths. The fluid sampling system further comprises a controller comprising at least one processor configured to execute coded instructions stored in memory of the controller. The coded instructions, when executed by the at least one processor, cause the processor to: receive the raw data relating to the optical properties of the fluid from the spectrometer; and predict percentage levels of one or more components in the fluid based at least in part on the raw data relating to the optical properties of the fluid, wherein the one or more components comprise at least one gas component without an optical signature in the near infrared spectrum.

In another example embodiment, the fluid sampling system comprises coded instructions, that when executed by the at least one processor, cause the processor to: predict a partial mass density of the fluid based at least in part on the raw data relating to the optical properties of the fluid; predict an ideal mass density of the fluid based on an assumption that the fluid contains only hydrocarbons and carbon dioxide; compare the partial mass density to the ideal mass density to determine whether the one or more components comprise one or more non-hydrocarbon components based on a percentage difference between the partial mass density and the ideal mass density; and determine a mole fraction of the one or more non-hydrocarbon components based on the percentage difference.

In another example embodiment, the fluid sampling system comprises coded instructions, that when executed by the at least one processor, cause the processor to: predict an optics-based mass density of the fluid based at least in part on the raw data relating to the optical properties of the fluid; predict compositions of the one or more components in the fluid; use an equation of state (EOS) model to predict an EOS-based mass density based at least in part on the predicted compositions of the one or more components in the fluid, pressure of the fluid, and temperature of the fluid; and compare the optics-based mass density to the EOS-based mass density to determine whether the one or more components comprise one or more non-hydrocarbon components based on a percentage difference between the optics-based mass density and the EOS-based mass density.

In another example embodiment, the fluid sampling system comprises coded instructions, that when executed by the at least one processor, cause the processor to: predict a first optics-based mass density of the fluid based at least in part on the raw data relating to the optical properties of the fluid; predict a second optics-based mass density of the fluid based at least in part on the raw data relating to the optical properties of the fluid, wherein predicting the second optics-based mass density comprises normalizing the raw data relating to the optical properties of the fluid to one or more hydrocarbon frequency channels; and compare the first optics-based mass density to the second optics-based mass density to determine whether the one or more components comprise one or more non-hydrocarbon components based on a percentage difference between the first optics-based mass density and the second optics-based mass density.

In another example embodiment, the fluid sampling system comprises coded instructions, that when executed by the at least one processor, cause the processor to convert the mole fraction of the one or more non-hydrocarbon components to a mass fraction of the one or more non-hydrocarbon components if the one or more non-hydrocarbon components are known.

In another example embodiment, the fluid sampling system comprises coded instructions, that when executed by the at least one processor, cause the processor to: predict compositions of the one or more components in the fluid; predict the data relating to the optical properties of the fluid, pressure of the fluid, and temperature of the fluid based at least in part on the compositions of the one or more components of the fluid, pressure of the fluid, and temperature of the fluid; compare the predicted data relating to the optical properties of the fluid to the raw data relating to the optical properties of the fluid to determine whether the one or more components comprise one or more non-hydrocarbon components based on a percentage difference between the predicted data relating to the optical properties of the fluid and the raw data relating to the optical properties of the fluid; and determine a mole fraction of the one or more non-hydrocarbon components based on the percentage difference.

In another example embodiment, the fluid sampling system comprises coded instructions, that when executed by the at least one processor, cause the processor to convert the mole fraction of the one or more non-hydrocarbon components to a mass fraction of the one or more non-hydrocarbon components if the one or more non-hydrocarbon components are known.

In another example embodiment, the fluid sampling system comprises coded instructions, that when executed by the at least one processor, cause the processor to: predict compositions of the one or more components in the fluid; calculate an average molecular weight of one or more known components in the fluid; use a partial least squares (PLS) to predict a mass density of the fluid based at least in part on the raw data relating to the optical properties of the fluid; calculate a number of moles of the one or more known components in the fluid by dividing the predicted mass density by the average molecular weight; determine a mole fraction of the one or more known components in the fluid based at least in part on the number of moles of the one or more known components in the fluid; calculate a number of moles of one or more unknown components in the fluid based at least in part on the mole fraction of the one or more known components in the fluid; and calculate a molecular weight of the one or more unknown components in the fluid based at least in part on the number of moles of one or more unknown components in the fluid.

In another example embodiment, the fluid sampling system comprises coded instructions, that when executed by the at least one processor, cause the processor to adjust one or more operating parameters of the oil and gas well operation based at least in part on the percentage levels of one or more components in the fluid.

In another example embodiment, the fluid sampling tool comprises the controller.

In one example embodiment of the disclosure, a method is provided. The method comprises: disposing a fluid sampling tool within a wellbore; drawing fluid from a formation within the wellbore, within which the fluid sampling tool is disposed, using a probe; detecting raw data relating to optical properties of the fluid using a spectrometer, wherein the raw data relating to the optical properties of the fluid comprises optical absorbance at a plurality of wavelengths; receiving, by a controller, the raw data relating to optical properties of the fluid from the spectrometer, wherein the controller comprises at least one processor configured to execute coded instruction stored in a memory of the controller; and predicting, by the controller, percentage levels of one or more components in the fluid based at least in part on the raw data relating to the optical properties of the fluid, wherein the one or more components comprise at least one gas component without an optical signature in the near infrared spectrum.

In another example embodiment, the method comprises: predicting a partial mass density of the fluid based at least in part on the raw data relating to the optical properties of the fluid; predicting an ideal mass density of the fluid based on an assumption that the fluid contains only hydrocarbons and carbon dioxide; comparing the partial mass density to the ideal mass density to determine whether the one or more components comprise one or more non-hydrocarbon components based on a percentage difference between the partial mass density and the ideal mass density; and determining a mole fraction of the one or more non-hydrocarbon components based on the percentage difference.

In another example embodiment, the method comprises: predicting an optics-based mass density of the fluid based at least in part on the raw data relating to the optical properties of the fluid; predicting compositions of the one or more components in the fluid; using an equation of state (EOS) model to predict an EOS-based mass density based at least in part on the predicted compositions of the one or more components in the fluid, pressure of the fluid, and temperature of the fluid; and comparing the optics-based mass density to the EOS-based mass density to determine whether the one or more components comprise one or more non-hydrocarbon components based on a percentage difference between the optics-based mass density and the EOS-based mass density.

In another example embodiment, the method comprises: predicting a first optics-based mass density of the fluid based at least in part on the raw data relating to the optical properties of the fluid; predicting a second optics-based mass density of the fluid based at least in part on the raw data relating to the optical properties of the fluid, wherein predicting the second optics-based mass density comprises normalizing the raw data relating to the optical properties of the fluid to one or more hydrocarbon frequency channels; and comparing the first optics-based mass density to the second optics-based mass density to determine whether the one or more components comprise one or more non-hydrocarbon components based on a percentage difference between the first optics-based mass density and the second optics-based mass density.

In another example embodiment, the method comprises: converting the mole fraction of the one or more non-hydrocarbon components to a mass fraction of the one or more non-hydrocarbon components if the one or more non-hydrocarbon components are known.

In another example embodiment, the method comprises: predicting compositions of the one or more components in the fluid; predicting the data relating to the optical properties of the fluid, pressure of the fluid, and temperature of the fluid based at least in part on the compositions of the one or more components of the fluid, pressure of the fluid, and temperature of the fluid; comparing the predicted data relating to the optical properties of the fluid to the raw data relating to the optical properties of the fluid to determine whether the one or more components comprise one or more non-hydrocarbon components based on a percentage difference between the predicted data relating to the optical properties of the fluid and the raw data relating to the optical properties of the fluid; and determining a mole fraction of the one or more non-hydrocarbon components based on the percentage difference.

In another example embodiment, the method comprises: converting the mole fraction of the one or more non-hydrocarbon components to a mass fraction of the one or more non-hydrocarbon components if the one or more non-hydrocarbon components are known.

In another example embodiment, the method comprises: predicting compositions of the one or more components in the fluid; calculating an average molecular weight of one or more known components in the fluid; using a partial least squares (PLS) to predict a mass density of the fluid based at least in part on the raw data relating to the optical properties of the fluid; calculating a number of moles of the one or more known components in the fluid by dividing the predicted mass density by the average molecular weight; determining a mole fraction of the one or more known components in the fluid based at least in part on the number of moles of the one or more known components in the fluid; calculating a number of moles of one or more unknown components in the fluid based at least in part on the mole fraction of the one or more known components in the fluid; and calculating a molecular weight of the one or more unknown components in the fluid based at least in part on the number of moles of one or more unknown components in the fluid.

In another example embodiment, the method comprises: adjusting one or more operating parameters of the oil and gas well operation based at least in part on the percentage levels of one or more components in the fluid.

While embodiments have been described herein, those skilled in the art, having benefit of this disclosure, will appreciate that other embodiments are envisioned that do not depart from the inventive scope. Accordingly, the scope of the present claims or any subsequent claims shall not be unduly limited by the description of the embodiments described herein.

The techniques presented and claimed herein are referenced and applied to material objects and concrete examples of a practical nature that demonstrably improve the present technical field and, as such, are not abstract, intangible or purely theoretical. Further, if any claims appended to the end of this specification contain one or more elements designated as "means for [perform]ing [a function] . . . " or "step for [perform]ing [a function] . . . ", it is intended that such elements are to be interpreted under 35 U.S.C. § 112(f). However, for any claims containing elements designated in any other manner, it is intended that such elements are not to be interpreted under 35 U.S.C. § 112(f).

What is claimed is:

1. A fluid sampling system, comprising:
a fluid sampling tool comprising:
a probe configured to draw a fluid from a formation within which the fluid sampling tool is disposed during an oil and gas well operation; and
a spectrometer configured to detect raw data relating to optical properties of the fluid, wherein the raw data relating to the optical properties of the fluid comprises optical absorbance at a plurality of wavelengths; and
a controller comprising at least one processor configured to execute coded instructions stored in memory of the controller, wherein the coded instructions, when executed by the at least one processor, cause the processor to:
receive the raw data relating to the optical properties of the fluid from the spectrometer;
predict percentage levels of one or more components in the fluid based at least in part on the raw data relating to the optical properties of the fluid, wherein the one or more components comprise at least one gas component without an optical signature in the near infrared spectrum;
predict a partial mass density of the fluid based at least in part on the raw data relating to the optical properties of the fluid;
predict an ideal mass density of the fluid based on an assumption that the fluid contains only hydrocarbons and carbon dioxide;
compare the partial mass density to the ideal mass density to determine whether the one or more components comprise one or more non-hydrocarbon components based on a percentage difference between the partial mass density and the ideal mass density; and
determine a mole fraction of the one or more non-hydrocarbon components based on the percentage difference.

2. The fluid sampling system of claim 1, wherein the coded instructions, when executed by the at least one processor, cause the processor to:

predict an optics-based mass density of the fluid based at least in part on the raw data relating to the optical properties of the fluid;
predict compositions of the one or more components in the fluid;
use an equation of state (EOS) model to predict an EOS-based mass density based at least in part on the predicted compositions of the one or more components in the fluid, pressure of the fluid, and temperature of the fluid; and
compare the optics-based mass density to the EOS-based mass density to determine whether the one or more components comprise one or more non-hydrocarbon components based on a percentage difference between the optics-based mass density and the EOS-based mass density.

3. The fluid sampling system of claim 1, wherein the coded instructions, when executed by the at least one processor, cause the processor to:
predict a first optics-based mass density of the fluid based at least in part on the raw data relating to the optical properties of the fluid;
predict a second optics-based mass density of the fluid based at least in part on the raw data relating to the optical properties of the fluid, wherein predicting the second optics-based mass density comprises normalizing the raw data relating to the optical properties of the fluid to one or more hydrocarbon frequency channels; and
compare the first optics-based mass density to the second optics-based mass density to determine whether the one or more components comprise one or more non-hydrocarbon components based on a percentage difference between the first optics-based mass density and the second optics-based mass density.

4. The fluid sampling system of claim 3, wherein the coded instructions, when executed by the at least one processor, cause the processor to convert the mole fraction of the one or more non-hydrocarbon components to a mass fraction of the one or more non-hydrocarbon components if the one or more non-hydrocarbon components are known.

5. The fluid sampling system of claim 1, wherein the coded instructions, when executed by the at least one processor, cause the processor to convert the mole fraction of the one or more non-hydrocarbon components to a mass fraction of the one or more non-hydrocarbon components if the one or more non-hydrocarbon components are known.

6. The fluid sampling system of claim 1, wherein the coded instructions, when executed by the at least one processor, cause the processor to adjust one or more operating parameters of the oil and gas well operation based at least in part on the percentage levels of one or more components in the fluid.

7. The fluid sampling system of claim 1, wherein the fluid sampling tool comprises the controller.

8. A method comprising:
disposing a fluid sampling tool within a wellbore;
drawing fluid from a formation within the wellbore, within which the fluid sampling tool is disposed, using a probe;
detecting raw data relating to optical properties of the fluid using a spectrometer, wherein the raw data relating to the optical properties of the fluid comprises optical absorbance at a plurality of wavelengths;
receiving, by a controller, the raw data relating to optical properties of the fluid from the spectrometer, wherein the controller comprises at least one processor configured to execute coded instruction stored in a memory of the controller;

predicting, by the controller, percentage levels of one or more components in the fluid based at least in part on the raw data relating to the optical properties of the fluid, wherein the one or more components comprise at least one gas component without an optical signature in the near infrared spectrum;

predicting a partial mass density of the fluid based at least in part on the raw data relating to the optical properties of the fluid;

predicting an ideal mass density of the fluid based on an assumption that the fluid contains only hydrocarbons and carbon dioxide;

comparing the partial mass density to the ideal mass density to determine whether the one or more components comprise one or more non-hydrocarbon components based on a percentage difference between the partial mass density and the ideal mass density; and determining a mole fraction of the one or more non-hydrocarbon components based on the percentage difference.

9. The method of claim 8, further comprising:

predicting an optics-based mass density of the fluid based at least in part on the raw data relating to the optical properties of the fluid;

predicting compositions of the one or more components in the fluid;

using an equation of state (EOS) model to predict an EOS-based mass density based at least in part on the predicted compositions of the one or more components in the fluid, pressure of the fluid, and temperature of the fluid; and comparing the optics-based mass density to the EOS-based mass density to determine whether the one or more components comprise one or more non-hydrocarbon components based on a percentage difference between the optics-based mass density and the EOS-based mass density.

10. The method of claim 8, further comprising:

predicting a first optics-based mass density of the fluid based at least in part on the raw data relating to the optical properties of the fluid;

predicting a second optics-based mass density of the fluid based at least in part on the raw data relating to the optical properties of the fluid, wherein predicting the second optics-based mass density comprises normalizing the raw data relating to the optical properties of the fluid to one or more hydrocarbon frequency channels; and comparing the first optics-based mass density to the second optics-based mass density to determine whether the one or more components comprise one or more non-hydrocarbon components based on a percentage difference between the first optics-based mass density and the second optics-based mass density.

11. The method of claim 10, further comprising:

converting the mole fraction of the one or more non-hydrocarbon components to a mass fraction of the one or more non-hydrocarbon components if the one or more non-hydrocarbon components are known.

12. The method of claim 8, further comprising:

converting the mole fraction of the one or more non-hydrocarbon components to a mass fraction of the one or more non-hydrocarbon components if the one or more non-hydrocarbon components are known.

13. The method of claim 8, further comprising:

adjusting one or more operating parameters of the oil and gas well operation based at least in part on the percentage levels of one or more components in the fluid.

14. The method of claim 8, wherein the fluid sampling tool comprises the controller.

15. A fluid sampling system, comprising:

a fluid sampling tool comprising:

a probe configured to draw a fluid from a formation within which the fluid sampling tool is disposed during an oil and gas well operation; and a spectrometer configured to detect raw data relating to optical properties of the fluid, wherein the raw data relating to the optical properties of the fluid comprises optical absorbance at a plurality of wavelengths; and a controller comprising at least one processor configured to execute coded instructions stored in memory of the controller, wherein the coded instructions, when executed by the at least one processor, cause the processor to:

receive the raw data relating to the optical properties of the fluid from the spectrometer;

predict percentage levels of one or more components in the fluid based at least in part on the raw data relating to the optical properties of the fluid, wherein the one or more components comprise at least one gas component without an optical signature in the near infrared spectrum;

predict compositions of the one or more components in the fluid;

predict data relating to the optical properties of the fluid, pressure of the fluid, and temperature of the fluid based at least in part on the compositions of the one or more components of the fluid, pressure of the fluid, and temperature of the fluid;

compare the predicted data relating to the optical properties of the fluid to the raw data relating to the optical properties of the fluid to determine whether the one or more components comprise one or more non-hydrocarbon components based on a percentage difference between the predicted data relating to the optical properties of the fluid and the raw data relating to the optical properties of the fluid; and determine a mole fraction of the one or more non-hydrocarbon components based on the percentage difference.

16. A method comprising:

disposing a fluid sampling tool within a wellbore;

drawing fluid from a formation within the wellbore, within which the fluid sampling tool is disposed, using a probe;

detecting raw data relating to optical properties of the fluid using a spectrometer, wherein the raw data relating to the optical properties of the fluid comprises optical absorbance at a plurality of wavelengths;

receiving, by a controller, the raw data relating to optical properties of the fluid from the spectrometer, wherein the controller comprises at least one processor configured to execute coded instruction stored in a memory of the controller;

predicting, by the controller, percentage levels of one or more components in the fluid based at least in part on the raw data relating to the optical properties of the fluid, wherein the one or more components comprise at least one gas component without an optical signature in the near infrared spectrum;

predicting compositions of the one or more components in the fluid;

predicting data relating to the optical properties of the fluid, pressure of the fluid, and temperature of the fluid based at least in part on the compositions of the one or more components of the fluid, pressure of the fluid, and temperature of the fluid;

comparing the predicted data relating to the optical properties of the fluid to the raw data relating to the optical properties of the fluid to determine whether the one or more components comprise one or more non-hydrocarbon components based on a percentage difference between the predicted data relating to the optical properties of the fluid and the raw data relating to the optical properties of the fluid; and determining a mole fraction of the one or more non-hydrocarbon components based on the percentage difference.

* * * * *